United States Patent [19]
Kami et al.

[11] Patent Number: 5,339,799
[45] Date of Patent: Aug. 23, 1994

[54] MEDICAL SYSTEM FOR REPRODUCING A STATE OF CONTACT OF THE TREATMENT SECTION IN THE OPERATION UNIT

[75] Inventors: Kuniaki Kami; Hideyuki Adachi, both of Hachioji; Koichi Umeyama, Kasukabe; Yoshihiro Kosaka, Hachioji; Seiji Yamaguchi, Hachioji; Eiichi Fuse, Hachioji; Michio Sato, Hino; Masakazu Nakamura, Hachioji; Yasundo Tanaka, Urawa; Takashi Fukaya, Hachioji; Kiyotaka Matsuno, Hachioji; Katsuya Suzuki, Hachioji, all of Japan

[73] Assignee: Olympus Optical Co., Ltd., Tokyo, Japan

[21] Appl. No.: 870,338

[22] Filed: Apr. 17, 1992

[30] Foreign Application Priority Data

Apr. 23, 1991 [JP] Japan .................. 3-092236
Apr. 24, 1991 [JP] Japan .................. 3-094455
Jul. 24, 1991 [JP] Japan .................. 3-184897

[51] Int. Cl.$^5$ .................. A61B 1/00; A61B 10/00
[52] U.S. Cl. .................. 128/4; 128/751; 128/6; 606/205; 606/167
[58] Field of Search .................. 128/774, 739, 4-6, 128/751, 755; 73/866.5, 865.7, 865.8; 901/33, 34; 340/407; 434/112, 175, 275; 414/2, 4, 5, 730, 740; 606/205, 206, 207

[56] References Cited

U.S. PATENT DOCUMENTS

| | | | |
|---|---|---|---|
| 3,742,935 | 7/1973 | Baessler et al. | 434/275 |
| 4,302,138 | 11/1981 | Zarudiansky | 901/33 |
| 4,469,091 | 9/1984 | Slanetz, Jr. | 128/6 |
| 4,655,673 | 4/1987 | Hawkes | 414/5 |
| 4,982,725 | 1/1991 | Hibino et al. | 128/4 |
| 5,116,180 | 5/1992 | Fung et al. | 414/5 |
| 5,142,930 | 9/1992 | Allen et al. | 414/4 |

FOREIGN PATENT DOCUMENTS

| | | |
|---|---|---|
| 61-9615 | 1/1986 | Japan . |
| 61-65903 | 5/1986 | Japan . |
| 61-87529 | 5/1986 | Japan . |
| 61-87530 | 5/1986 | Japan . |
| 61-92650 | 5/1986 | Japan . |
| 62-166312 | 7/1987 | Japan . |
| 1-221134 | 9/1989 | Japan . |
| 2-55907 | 4/1990 | Japan . |
| 3-68327 | 3/1991 | Japan . |
| 3-97430 | 4/1991 | Japan . |
| 3-198828 | 8/1991 | Japan . |

*Primary Examiner*—Richard J. Apley
*Assistant Examiner*—John P. Leubecker
*Attorney, Agent, or Firm*—Armstrong, Westerman, Hattori, McLeland & Naughton

[57] ABSTRACT

A medical system according to the present invention comprises a medical apparatus including an operation unit manipulated by a surgeon and a treatment section formed away from the operation unit for treating a subject, a detector or a pressure sensor for detecting a state of contact between the subject and the treatment section, and a reproduction mechanism for amplifying a small contact pressure according to the output of the detector and thus reproduce the state of contact so that the surgeon can perceive the state of contact.

15 Claims, 35 Drawing Sheets

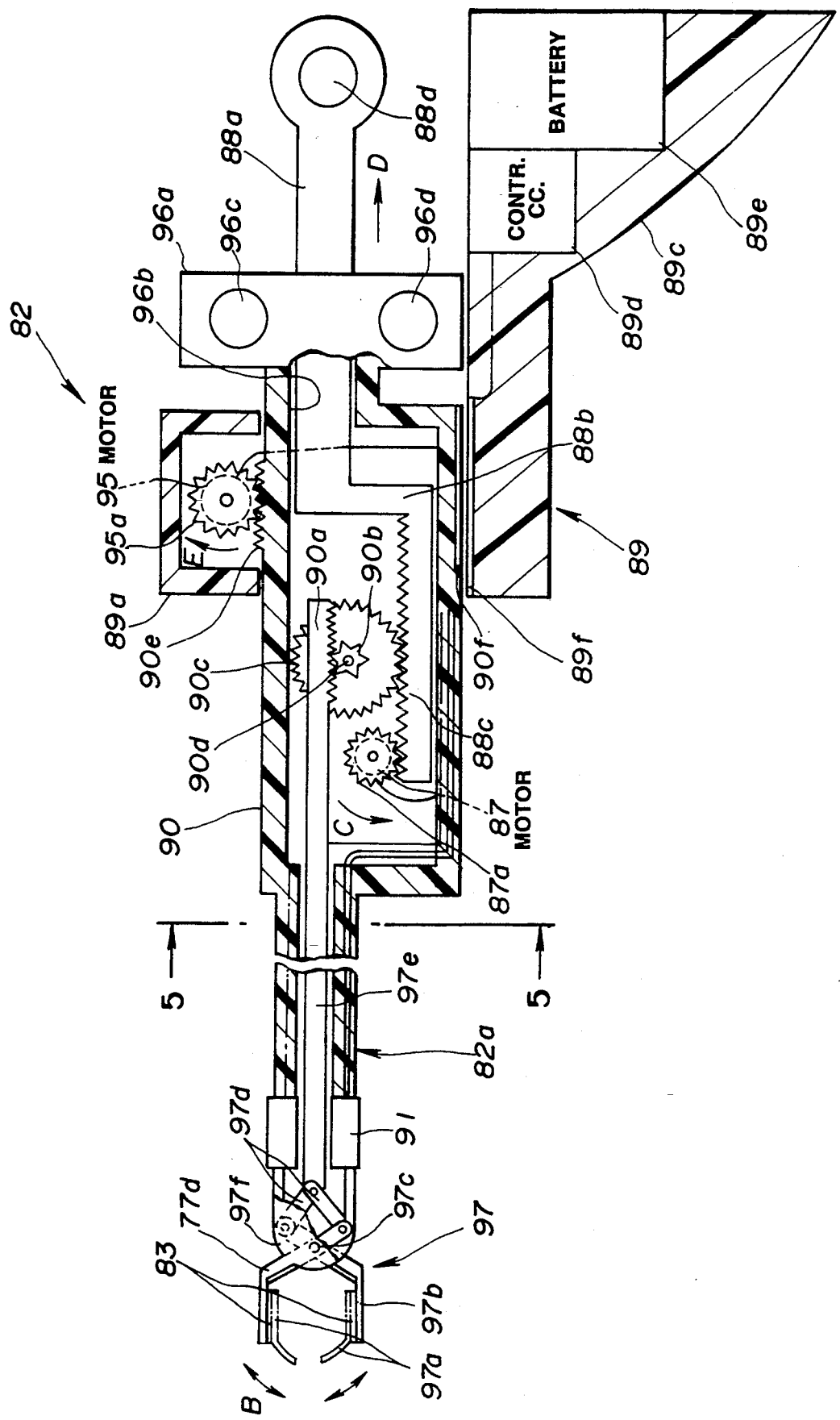

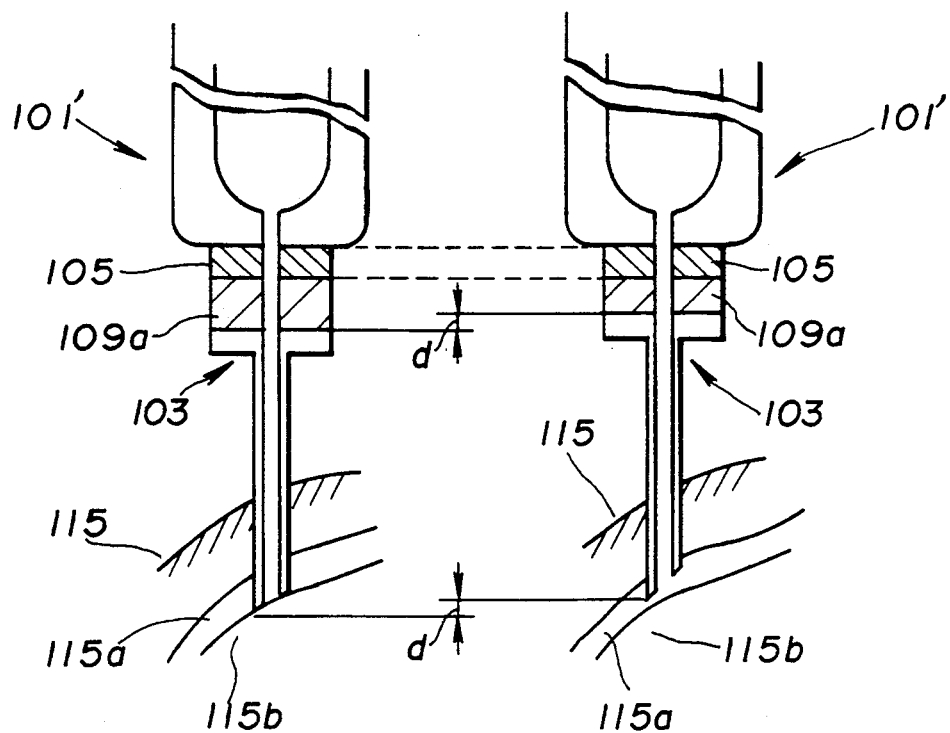
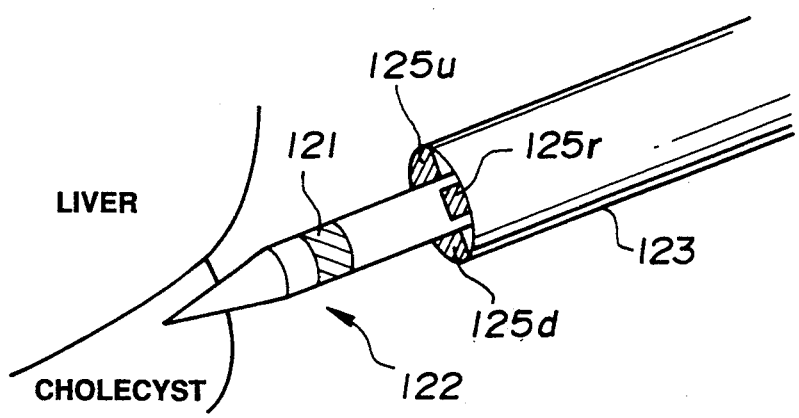

FIG. 57(A)
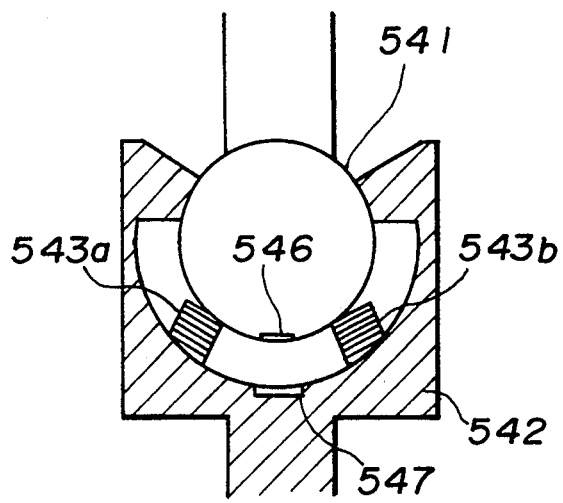
FIG. 57(B)
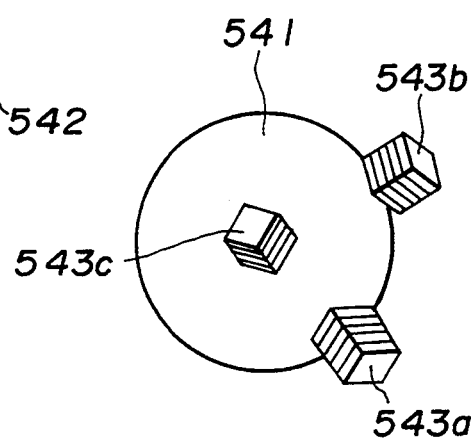
FIG. 58(A) FIG. 58(B) FIG. 58(C)
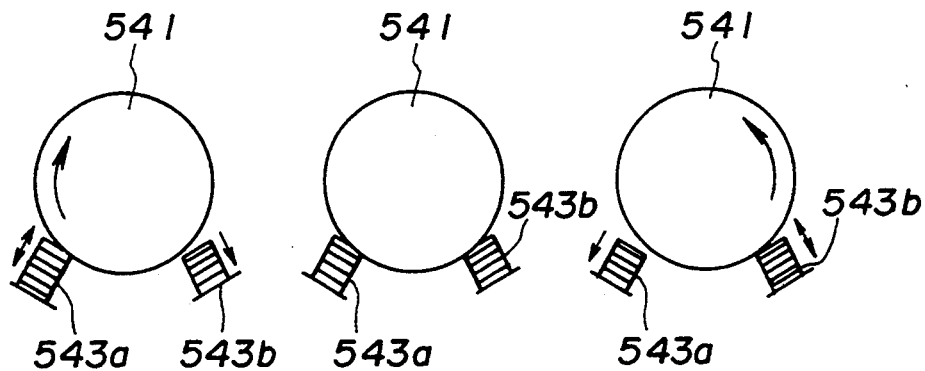

MEDICAL SYSTEM FOR REPRODUCING A STATE OF CONTACT OF THE TREATMENT SECTION IN THE OPERATION UNIT

BACKGROUND OF THE INVENTION

1. Field of the Invention

The present invention relates to a medical system having a reproduction means for detecting a state of contact of a treatment section formed at the distal end of a medical apparatus for treating a subject and reproducing the state of contact in an operation unit a surgeon manipulates so that the surgeon can perceive the state of contact.

2. Description of the Related Art

Endoscopes have been adopted widely in the field of medicine in recent years, wherein an observation means or imaging means is installed at the end (distal end) of an elongated insertion tube and an eyepiece unit formed at the back (proximal end) of the insertion tube or a monitor is used for observation. These endoscopes obviate dissection but permit treatment with a treatment adapter inserted into a channel, if necessary.

Instead of dissection, a small hole is formed in the abdomen to insert an endoscope or a treatment adapter. Then, the treatment adapter is used to allow surgery to proceed under endoscopic observation.

Under microscopic observation, a delicate surgical procedure may be carried out.

In the foregoing medical apparatus, an operation unit manipulated with a hand is separated from a treatment section for treating a subject, and a state of contact between the treatment section and the subject is not conveyed to a surgeon (operation unit). Moreover, a moving rate of the treatment section must be very small or delicate to achieve treatment. Accordingly, a manipulation rate or a manipulation force for manipulating the operation unit must be drastically lessened to realize precise treatment.

For example, when delicate treatment is required, a contact pressure of a treatment section in contact with a subject is so small that it is very difficult to recognize the state of contact correctly.

A surgeon hardly can reduce a moving rate or a moving force of his/her own hand according to the size of a region to be treated. The medical apparatus of the prior art sometimes fails to provide preferable treatment.

SUMMARY OF THE INVENTION

The objects of the present invention are to provide a medical system for permitting easy perception of the state of contact between a treatment section and a subject even when an operation unit and a treatment section are separated from each other, and to provide a medical system for permitting easy perception of the state of contact between a treatment section and a subject even when the subject to be treated is very small.

Other objects of the invention are to provide a medical system for offering medical care by operating a pseudo treatment section with a realistic feeling even when an operation unit and a treatment section are separated from each other, and to provide a medical system for offering medical care by operating a pseudo treatment section with a realistic feeling even when a subject to be treated is very small.

In a medical system 1 of the present invention shown in the conceptual configuration diagram of FIG. 1, a treated lesion 2 of a subject is treated using a treatment section 3a of a treatment means 3. The treatment means 3 is remotely connected to an operation unit 3c via a conversion means 3b. A surgeon 5 manipulates the operation unit 3c to operate the treatment section 3a. The state of operating the treatment section 3a against the treated lesion 2 is detected with a pressure sensor, a tactile sensor, or other sensor 6. A signal processing means 7 performs amplification and other processing. Then, the amplified signal drives a feeling reproduction means 8 formed in the operation unit 3. In association with the manipulation of the operation unit 3c, the feeling reproduction means 8 amplifies a contact pressure detected by the sensor 6 to reproduce the contact pressure so that the surgeon 5 will recognize the contact pressure tactilely. The feeling reproduction means 8 allows the surgeon 5 to perceive the state of operation, for example, that the treatment section 3a slightly touches the treated lesion 2 which cannot be perceived tactilely under a normal condition. Furthermore, the feeling reproduction means 8 will be helpful in delicate treatment. The signal processing means 7 can display information detected by the sensor 6 on a monitor 9.

BRIEF DESCRIPTION OF THE DRAWINGS

FIGS. 2 to 10 relate to the first embodiment of the present invention;

FIG. 2 is a block diagram showing the configuration of a control system of the first embodiment;

FIG. 3 is a lateral view showing a grasping forceps in the first embodiment;

FIG. 4 is a cross-sectional diagram showing the specific configuration of the grasping forceps;

FIG. 5 shows an 5—5 cross section of FIG. 4;

FIG. 7 is a lateral view showing a resecting section of the distal portion of a biopsy forceps;

FIG. 8 is a configuration diagram of an entire endoscope system having the biopsy forceps of FIG. 7;

FIG. 9 is a cross-sectional diagram showing the configuration of a variant of the grasping forceps of FIG. 4;

FIG. 10 is a block diagram showing the configuration of a control system of FIG. 9;

FIG. 11 is a configuration diagram of an entire medical system of the second embodiment;

FIGS. 13 to 17 relate to the third embodiment of the present invention;

FIG. 13 is a block diagram showing the configuration of a control system of the third embodiment;

FIG. 14 shows the configuration of an injector of the third embodiment;

FIG. 15 is an explanatory diagram showing a pressure sensor installed in the middle of a needle tip;

FIG. 16 is a block diagram of a variant of the control system of FIG. 13;

FIGS. 17(a) and 17(b) are explanatory diagrams of the operation of the variant;

FIGS. 18 to 21 relate to the fourth embodiment of the present invention;

FIG. 18 is an oblique view of the distal portion of a laser probe;

FIG. 19 is a block diagram showing the configuration of a control system;

FIG. 20 is an oblique view of the proximal portion of the laser probe;

FIG. 21 is an oblique view of the distal portion of a variant of the fourth embodiment;

FIG. 22 is a configuration diagram of a diathermic treatment apparatus;

FIG. 23 is an oblique view of an operation unit of the diathermic treatment apparatus;

FIG. 24 is a block diagram showing the configuration of a control system;

FIG. 26 is a block diagram showing the configuration of a diathermic treatment apparatus of the sixth embodiment;

FIG. 27 is a plan view of the distal portion of a diathermic snare;

FIG. 28 is a cross-sectional diagram of the distal portion of the diathermic snare;

FIG. 29 is a block diagram showing the configuration of the main section of the seventh embodiment;

FIG. 30 is a block diagram showing the configuration of a resistance detector;

FIG. 31 is a plan view of an operation unit on which a stopper is formed;

FIG. 32 shows the overall configuration of the eight embodiment;

FIG. 33 is a block diagram showing the configuration of a control;

FIG. 34 is an explanatory diagram showing a glove;

FIG. 35 is a block diagram showing the configuration of a control system of the ninth embodiment;

FIG. 36 shows the configuration of an optical system of the main unit of an intraoperative microscope;

FIG. 37 shows pseudo operation switches displayed within the observation field of view of the intraoperative microscope;

FIG. 38 is a lateral view of the intraoperative microscope;

FIG. 39 is a configuration diagram of an optical system in the main unit of an intraoperative microscope of the tenth embodiment;

FIG. 40 is a block diagram showing the configuration of a control section in the tenth embodiment;

FIG. 41 is an explanatory diagram showing pseudo operation switches displayed within the observation field of view of the intraoperative microscope;

FIG. 42 is a configuration diagram of an optical system in the main unit of an intraoperative microscope in the eleventh embodiment;

FIG. 43 is an explanatory diagram showing pseudo operation switches displayed within the observation field of view of the intraoperative microscope;

FIG. 44 is a configuration diagram showing an intraoperative microscope apparatus of the twelfth embodiment;

FIG. 45 is an oblique view of an operation unit of a needle holder;

FIG. 46 is an oblique view of a holding section of the needle holder;

FIG. 47 is a cross-sectional diagram showing the configuration of an air spring;

FIG. 48 is an oblique view of the configuration of an operating section;

FIG. 49 is a block diagram showing the configuration of a control section;

FIG. 50 is a frontal view of an intraoperative microscope of the thirteenth embodiment;

FIG. 51 is an oblique view showing the relationship between an operation unit and an operating section;

FIG. 52 is a configuration diagram of an intraoperative microscope of a variant of the thirteenth embodiment;

FIGS. 57(a) and 57(b) are explanatory diagrams showing the configuration of a joint of the intracorporeal treatment apparatus;

FIGS. 58(a), 58(b) and 58(c) are explanatory diagrams showing the movement of the joint;

DESCRIPTION OF THE PREFERRED EMBODIMENTS

Figure 1:
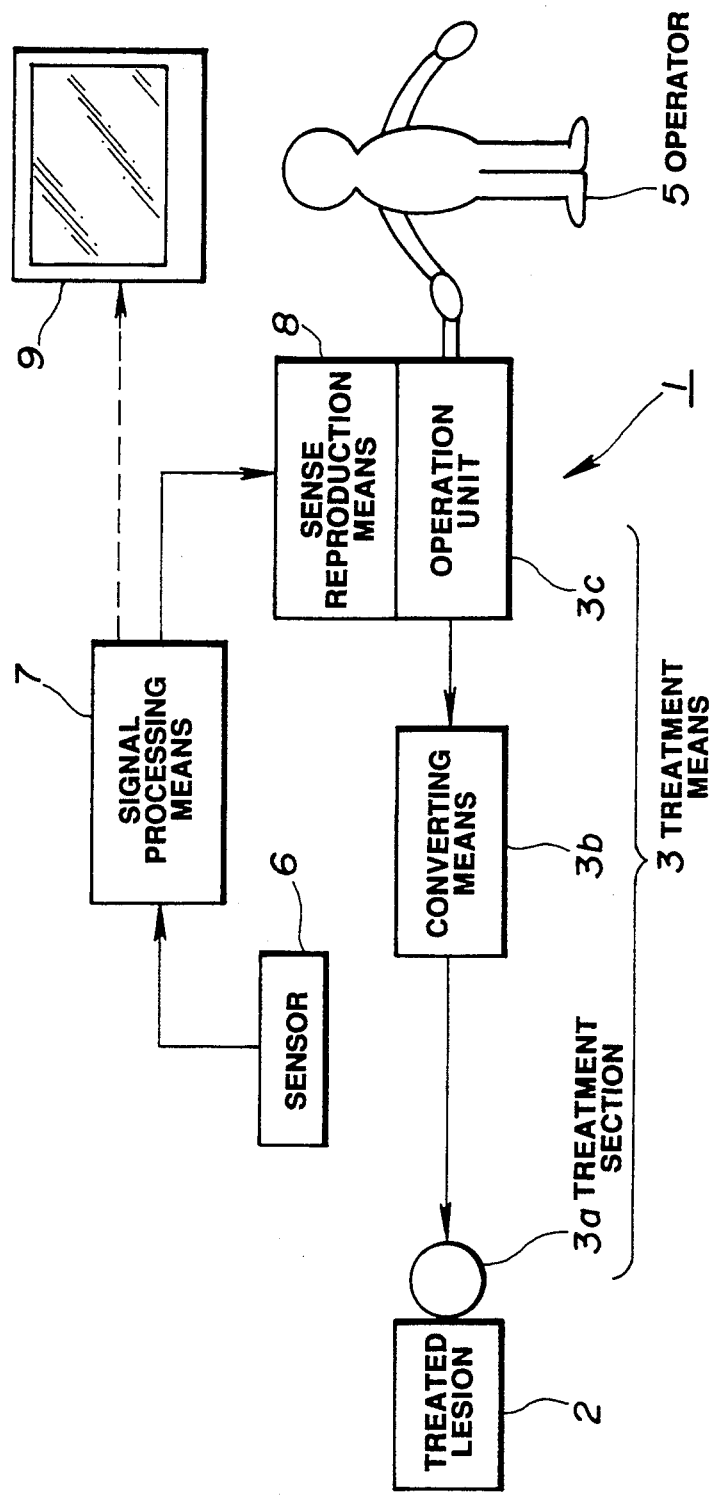
FIG. 1 is a block diagram showing the conceptual configuration of the present invention.
Figure 2:
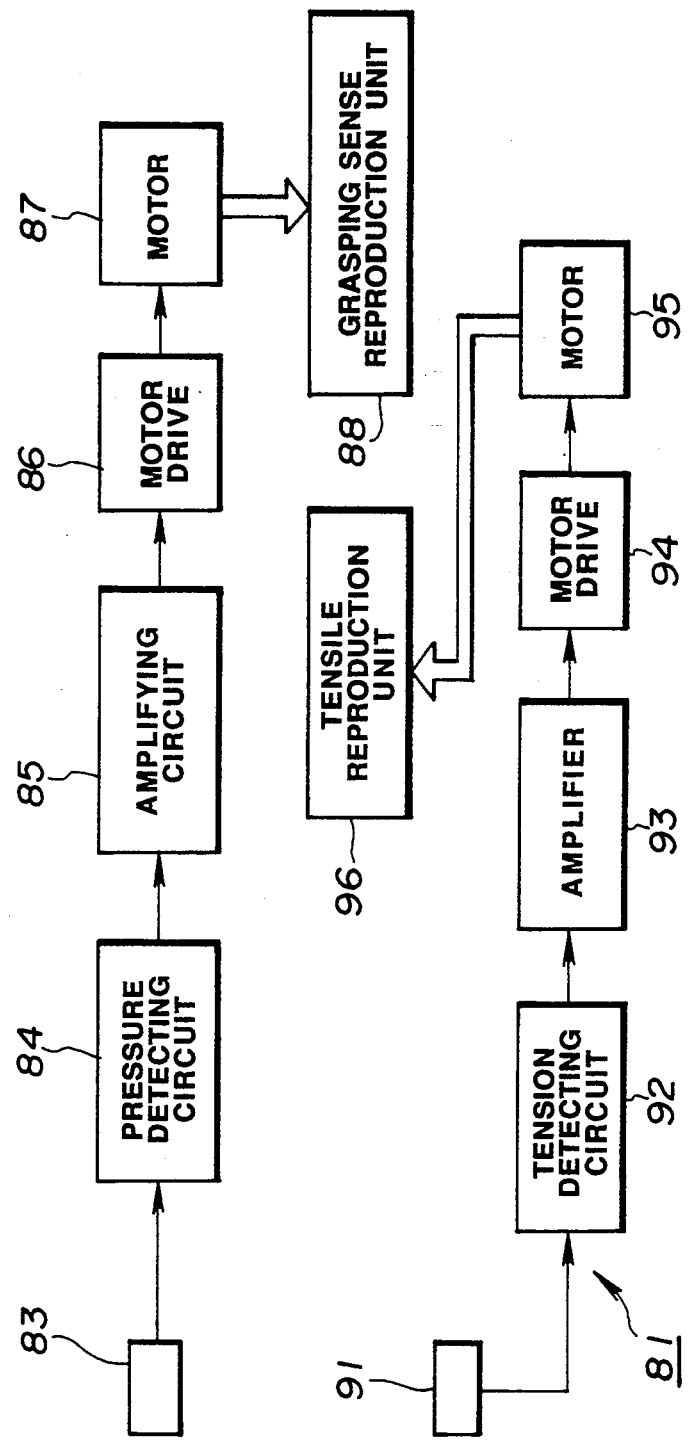

FIG. 2 shows a medical apparatus 81 having a grasping feeling reproduction facility of the first embodiment. In the medical apparatus 81, a grasping force detecting element 83 is incorporated in a grasping forceps (biopsy forceps) 82 shown in FIG. 3. The output of the grasping force detecting element 83 is supplied to a pressure detecting circuit 84 which, then, detects a grasping force. An amplifying circuit 85 amplifies the output signal. After that, a motor 87 is provided with drive current via a motor drive circuit 86.

The motor 87 drives a grasping feeling reproduction unit 88 of the grasping forceps. The grasping feeling reproduction unit 88 moves an operation knob 88a formed on an operation unit 89. The grasping forceps 82 is provided with a tension detecting element 91 for detecting a tension. The output of the tension detecting element 91 is supplied to a tension detecting circuit 92 which, then, detects a tension. An amplifying circuit 93 amplifies the tension signal. After that, a motor 95 is provided with motor current via a motor drive circuit 94. The motor 95 drives a tension reproduction unit 96. The tension reproduction unit 96 moves a slider 96a formed in the operation unit 89.

When it comes to the grasping forceps 82, a surgeon manipulates the operation knob 88a and slider 96a or, more particularly, moves the operation knob 88a back and forth relatively to the slider 96a capable of sliding on the body of the operation unit 89a. A force transmission member allows a grasping section 97 of the grasping forceps 82 serving as a treatment (operating) section open or close to grasp a subject. When the grasping section 97 grasps the subject, the grasping force detecting element 83 detects the grasping force. Then, the grasping feeling reproduction unit 88 is driven via the amplifying circuit 85. Thereby, the grasping force is amplified and reproduced in the operation knob 88a. The surgeon can recognize the degree of the grasping force tactilely.

An amplifying circuit 85 amplifies a weak signal so that a surgeon manipulating an operation knob 88 can feel the signal information. For example, when a surgeon opens or closes a grasping section 97 serving as a treatment section to grasp a subject, the surgeon is given a repulsive reaction force. Thus, the surgeon can check if he/she succeeds in grasping a polyp or other subject. A tension detecting element 91 for detecting a tension is formed near the tip of a grasping forceps 82. The tension detecting element 91 detects a tension occurring when a subject is grasped and pulled, then drives a tension reproduction unit 96 via an amplifying circuit 93. Eventually, a slider 96a moves back and forth.

For example, when pulling causes a resistive feeling or a heavy feeling, a reaction force occurs to pull back the slider 96a towards the subject. Thus, a surgeon tactilely perceives the state of tension occurring when the surgeon pulls off an subject. The amplifying circuit 93 amplifies a signal so that a surgeon can identify the signal information tactilely.

FIG. 4 shows the specific configuration of a grasping forceps 82 having the facility shown in FIG. 2. The grasping forceps 82 comprises an elongated insertion tube 82a, a grasping section 97 formed at the tip (end) of the insertion tube 82a, and an operation unit 89 formed in the proximal portion of the insertion tube 82a.

The grasping section 97 comprises a pair of jaws 97a, supports 97b whose distal portions are clamped on the proximal portions of the jaws 97a with grasping force detecting elements 83 interposed, a pivot 97c for supporting the proximal portions of a pair of supports 97b so that the supports 97b can swivel freely, and links 97d connected to the proximal ends of the supports 97b extending beyond the pivot 97c using pivotal members. The proximal ends of a pair of links 97d are connected to a flexible shaft 97e forming a manipulation force transmission means using a pivotal member. When the flexible shaft 97e is moved in the longitudinal direction, a pair of jaws 97a opens or closes, as shown with an arrow B.

The proximal portions of the supports 97b are placed in a slit formed on a semicircular portion of a distal member 97f. When the supports 97b swivel about the pivot 97c, the jaws 97a open or close. Grasping force detecting elements 83, which are interposed between the jaws 97a and supports 97b and formed with pressure sensors, are secured with adhesive on both sides to detect a pressure working on the jaws 97a.

The proximal portion of the distal member 97f is provided with, for example, a ring tension detection element 91 for detecting a tension working on the grasping section 97.

The flexible shaft 97e runs through a hollow insertion tube formation member, and the proximal portion of the flexible shaft 97e is encased in a conversion housing 90 accommodating a mechanism for converting a manipulation force which is formed in the front of the operation unit 89. The back of the conversion housing 90 is connected to a slider 96a via a guide bore 96b through which an operation knob 88a is routed to slide freely.

A rack 90a is formed at the proximal end of the flexible shaft 97e encased in the conversion housing 90. The rack 90a is engaged with a small first gear 90b. The first gear 90b is coupled to a large second gear 90c with an axis 90d as a center. The ends of the axis 90d are held on the conversion housing 90 to rotate freely. The second gear 90c is engaged with a rack 88c formed in the distal portion of an L-shaped operation bar 88b which is coupled to the operation knob 88a. A finger hole 88d is formed at the back of the operation knob 88a. Therefore, when the operation knob 88a is moved back and forth, the movement is transmitted to the flexible shaft 97e via the rack 88c, second gear 90c, first gear 90b, and rack 90a. Eventually, the flexible shaft 97e causes a pair of the jaws 79a to open or close.

Figure 6A:
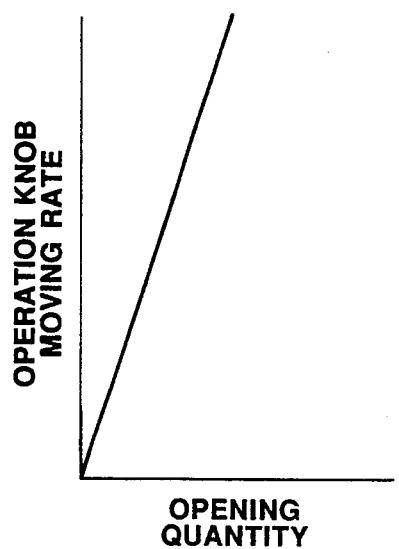
FIGS. 6(a) and 6(b) show characteristics representing the relationship between the manipulation rate of an operation knob for a grasping forceps and the operation rate of a grasping section.

The first gear 90b and second gear 90c are used to amplify an opening or closing rate of the jaws 97a and convert the amplified rate to a moving rate of the operation knob 88a. That is to say, as shown in FIG. 6a, a moving rate of the operation knob 88a is larger than an opening or closing rate of the jaws 97a. Therefore, a surgeon can generate a considerably larger moving rate than when he/she directly grasps a minute tissue. This makes grasping minute tissues more effortless.

Figure 6B:
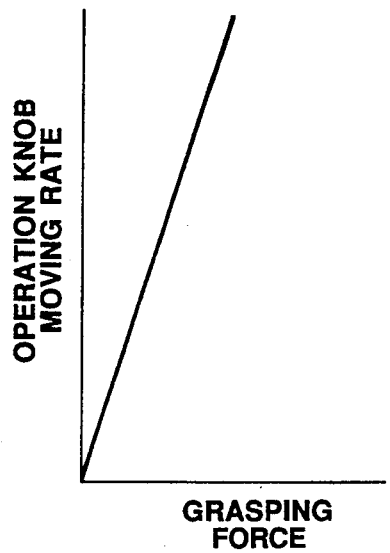

The conversion housing 90 further accommodates a grasping feeling reproducing mechanism. That is to say, a gear 87a mounted on the rotation axis of a motor 87 encased in the conversion housing 90 is engaged with a rack 88c coupled to an operation knob 88a. Then, when grasping force detection elements 83 detect a pressure, the motor 87 is driven in proportion to the pressure. The motor generates a rotation driving force for rotating the gear 87a counterclockwise indicated with an arrow C. The rotation driving force serves as a force for withdrawing the operation knob 88a, as indicated with an arrow D, and thus negating the manipulation for closing the jaws 97a (or advancing the operation knob 88a). Thus, a manipulation force control mechanism operates to provide a negative feedback for reducing a grasping force. The negative feedback manipulation force control mechanism realizes the relationship, for example, as shown in FIG. 6b, between the grasping force for grasping with the jaws 97a and the manipulation force for moving the operation knob 88a of the operation unit 89. The grasping force for grasping a tissue with the jaws 97a is associated with an amplified manipulation force. Thus, even a very weak grasping force is perceivable.

Assuming that a surgeon advances an operation knob 88a to close jaws 97a, when the jaws 97a grasp a tissue, a force of moving backward acts on the operation knob 88a according to the grasping force. The surgeon feels the force of moving backward to tactilely recognize the fact of grasping and the degree of the grasping force. When a motor 95 is not driven (or when grasping force detecting elements 83 detect no pressure), a gear 95a has almost no load and rotates freely.

Finger holes 96c and 96d are formed on a slider 96 connected to the conversion housing 90. In the body of an operation unit 89 into which the conversion housing 90 is fitted, a space is created to store a motor 95, for example, on the top of the conversion housing 90. Then, a tension reproduction mechanism is placed in the space. That is to say, a gear 95a mounted on the rotation axis of a motor 95 is engaged with a rack 90e formed on the external surface of the conversion housing 90. Then, when a tension detecting element 91 detects a tension, the motor 95 is driven with a force proportional to the tension. Then, a rotation driving force occurs to rotate the gear 95a clockwise as indicated with an arrow E. The rotation driving force acts as a force for advancing the slider 96a coupled to the conversion housing 90.

Specifically, an surgeon uses jaws 97a to grasp a tissue and pulls a grasping section 97 (withdraws a slider 96a and an operation knob 88a). Then, a tension detecting element 91 detects the tension. Thus, a tension control mechanism operates to provide a negative feedback appearing as a force for advancing the slider 96a. This allows the surgeon to tactilely perceive the fact that the tension is working and recognize the degree of the tension.

The gear 95a has almost no load to rotate freely when a motor 95 is not driven.

The body 89a of an operation unit has its bottom extended backward, thus forming a manipulation grip 89c which is gripped by a surgeon.

The grasping force detecting elements 83, tension detecting element 91, and motors 87 and 95 are connected to a control circuit 89d inside a chamber formed in the body 89a of an operation unit via leads. The control circuit 89d is made up of amplifying circuits 85 and 93, and motor drive circuits 86 and 94. A battery 89e for actuating the control circuit 89d is incorporated in the body 89a of the operation unit. The leads in a conversion housing are conducting electricity using sliding contacts 90f (See FIG. 5) formed in the longitudinal direction, and the leads in the body 89a of the operation unit, using contacts 89f opposing the sliding contacts 90f.

Figure 5:
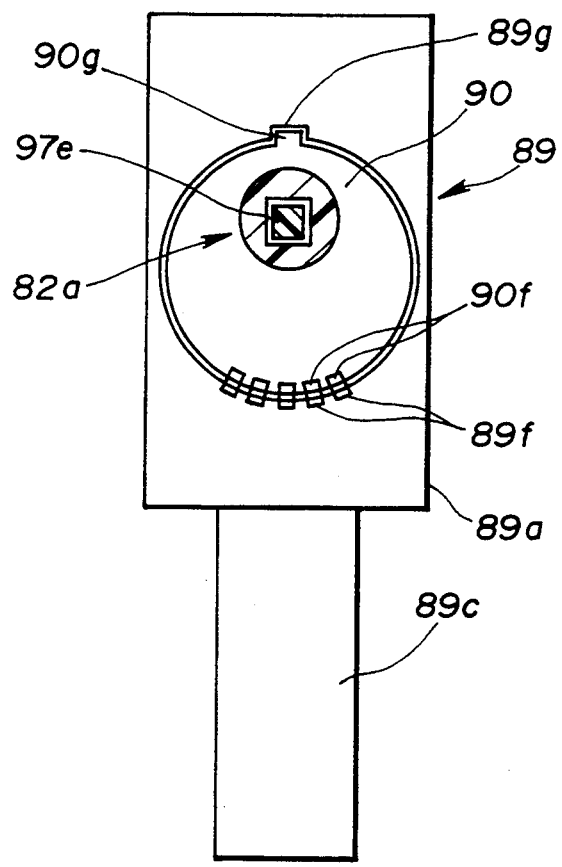

As shown in FIG. 5, the conversion housing 90 is provided with a projection 90g, and a linear ditch 89g is extending vertically in FIG. 5 in the body 89a of the operation unit. The projection 90g moves inside the linear ditch 89g; that is, in the longitudinal direction of an insertion tube 82a.

Figure 3:
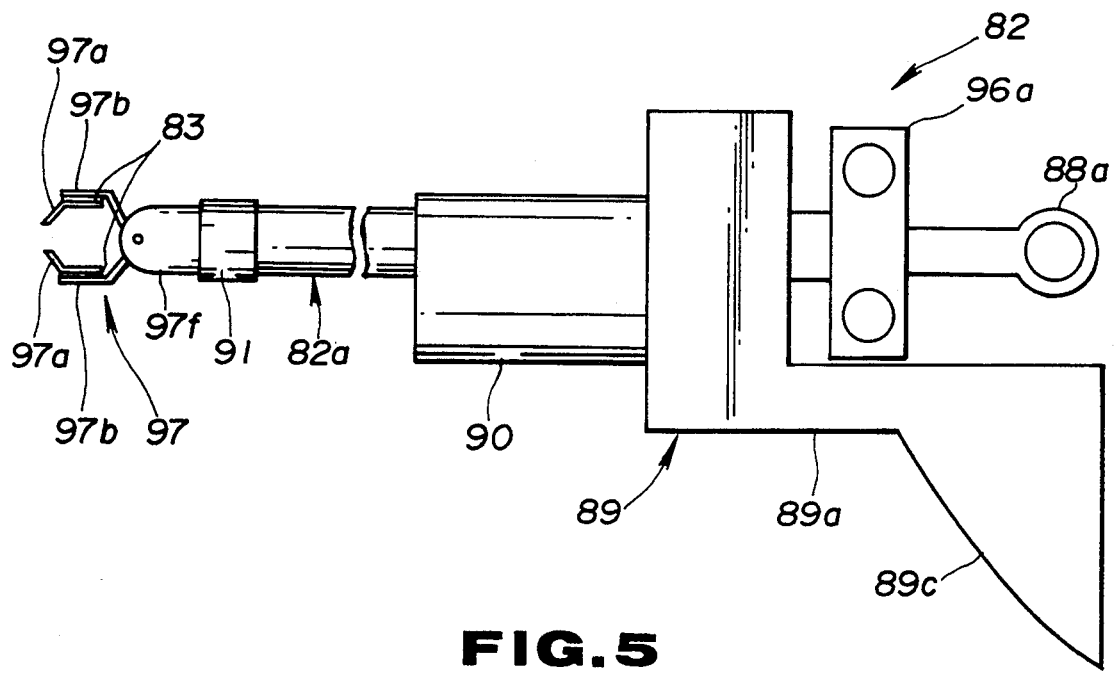

According to the aforesaid embodiment, a surgeon grasps an operation unit 89 as shown in FIG. 3, then withdraws an operation knob 88a with respect to a slider 96a. Thereby, jaws 97a open. Then, a grasping forceps 82 is moved towards a tissue to be grasped. The surgeon advances the operation knob 88a relatively to the slider 96a. Thereby, the jaws 97a close. With the closing, the tissue is grasped. The grasping force is detected by grasping force detecting elements 83, then reproduced as movement of the operation knob 88a. When a tension occurs, the tension is detected by a tension detection element 91, then reproduced as movement of the slider 88a. These movements are oriented reverse to the manipulated movement. These negative forces allow the surgeon to tactilely recognize the force working on the tissue.

According to this embodiment, when a grasping forceps 82 is operated, a surgeon can feel a delicate force variation occurring at the time of grasping. This is impossible in the prior art. When a treatment section in the distal portion of an operation unit 89 is actuated by manipulating an operation unit 89, the operation of the treatment section is fed back to the operation unit 89 with the operation force amplified. This permits delicate treatment.

Figure 7:
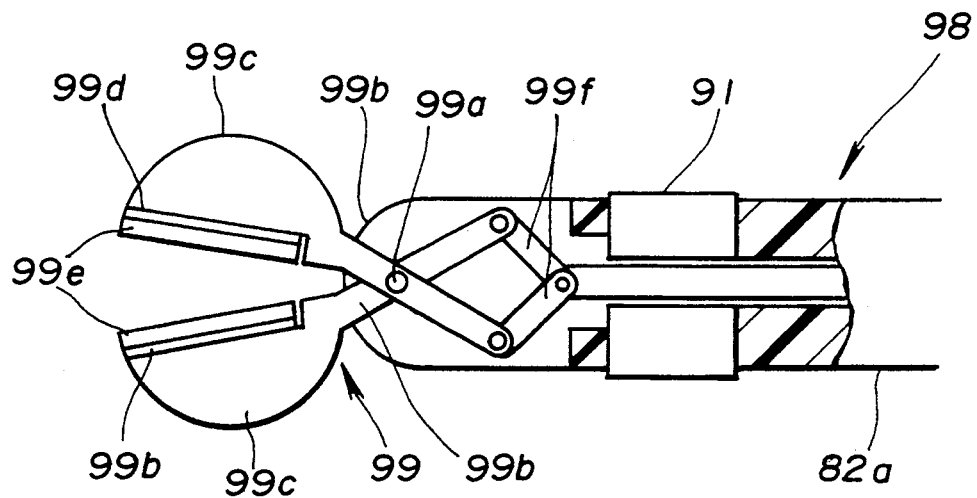

In FIGS. 3 and 4, a grasping forceps 82 having a grasping facility is used for explanation. A biopsy forceps 98 may have the same facility as shown in FIG. 7. In the biopsy forceps 98, a resecting section 99 for use in resection is formed as a treatment section at the tip of an insertion tube 82a. In the resecting section 99, semicircular cups 99c are formed as the distal portions of a pair of supports 99b which are supported with a pivot 99a to rotate freely. Sharp resection blades 99e are formed along the opening circumferences of the cups 99c with ring-type grasping force detecting elements 99d interposed. The proximal portions of the supports 99b are coupled to links 99f using pivotal members. A pair of links 99f is coupled to a flexible shaft using a pivotal member. Other components are identical to those shown in FIG. 4. The biopsy forceps 98 simplifies biopsy of minute tissues.

Figure 8:
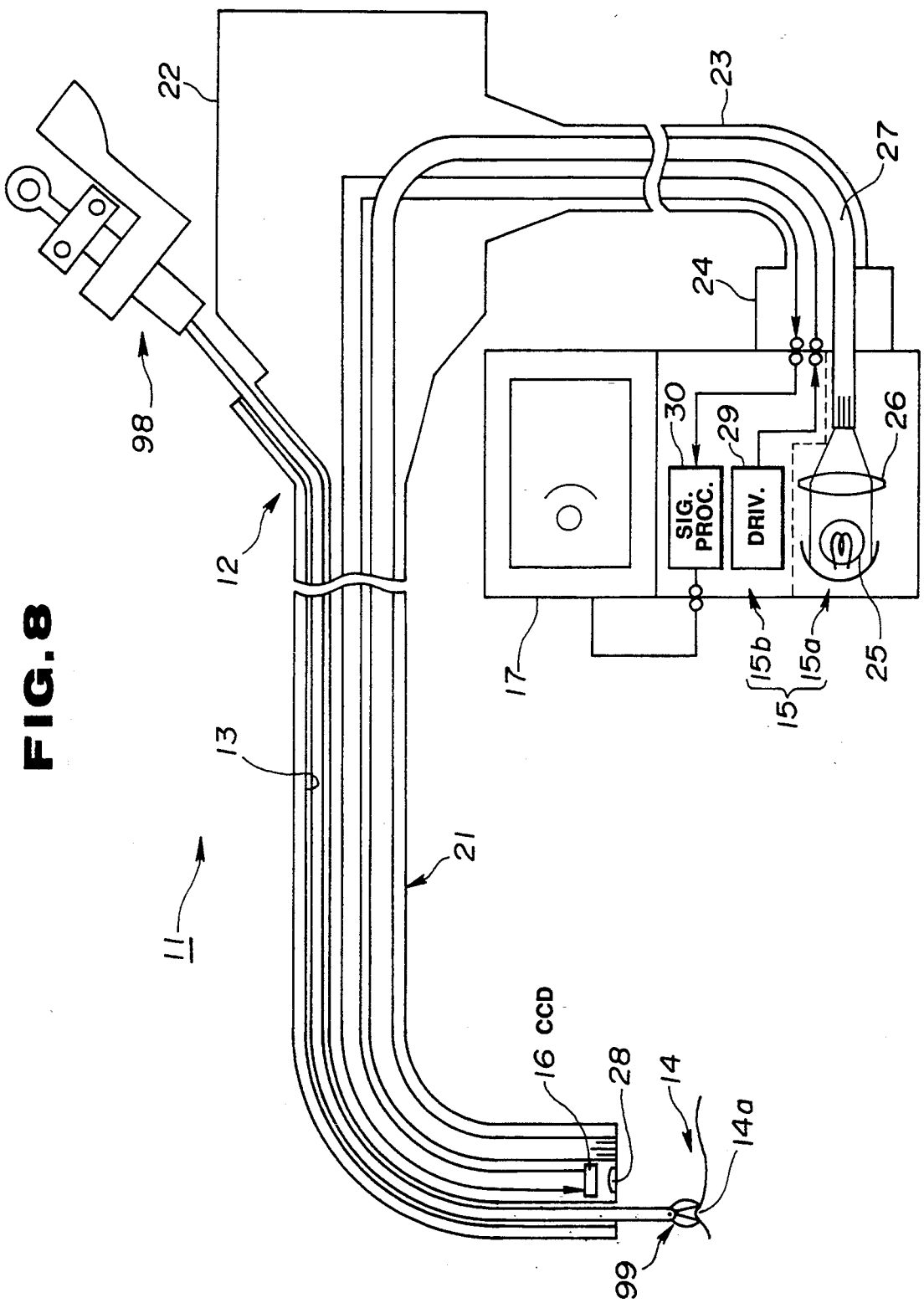

FIG. 8 shows an endoscope system 11 as an example of a medical system, wherein a biopsy forceps 98 is inserted into a channel 13 of an electronic endoscope 12 to biopsy (collect) a tissue 14a in an observed region of a living body.

The endoscope system 11 comprises the electronic endoscope 12 having a built-in imaging means, a light source 15a for supplying illumination light to the electronic endoscope, a video processor 15 having a built-in signal processing unit 15b for processing signals sent from a CCD 16 forming the imaging means, and a monitor 17 for displaying standard video signals the signal processing unit 15b generates.

The electronic endoscope 12 includes an elongated insertion tube 21, a large-diameter operation tube 22 formed proximally to the insertion tube, and a universal cable 23 extending outward from the side of the operation unit 22. A connector 24 formed at the tip of the universal cable 23 can be connected to the video processor 15.

When the connector 24 is connected, illumination light of a lamp 25 in the light source 15a is converged on a lens 26 and emitted to one end surface of a light guide 27. The light guide 27 transmits illumination light, then emits it forward from the end surface of the distal end of the insertion tube 21. An observed region 14 or a subject is illuminated with the emitted illumination light, then an objective 28 forms the optical image on a photoelectric-transfer surface of the CCD 16 arranged on the focal plane for the objective 28.

The optical image is photoelectrically transferred by the CCD 16, then read out from the CCD 16 with a drive signal sent from a drive circuit 29 to provide an image signal. The image signal is fed to a signal processing circuit 30. The signal processing circuit 30 generates a standard video signal. Then, the video signal displays the image of the observed region 14 on a monitor 17.

An surgeon observes the image displayed on the monitor 17 to evaluate the state of the observed region 14 (endoscopically). When endoscopic evaluation is unsatisfactory, a biopsy forceps 98 may be inserted into a channel 13. By manipulating a forceps operation unit 89, the surgeon can open a resecting section 99 to collect a tissue 14a under the observation through the electronic endoscope 12 (in this case, the surgeon observes the image of the resecting section 99 displayed on the monitor together with the image of the observed region 14). Using the biopsy forceps 98, even a minute tissue can be collected effortless. This eliminates accidental collection of an unnecessary tissue. Therefore, a living body will suffer an unnecessary trauma and recuperate quickly.

Furthermore, this embodiment permits delicate strip biopsy.

Figure 9:
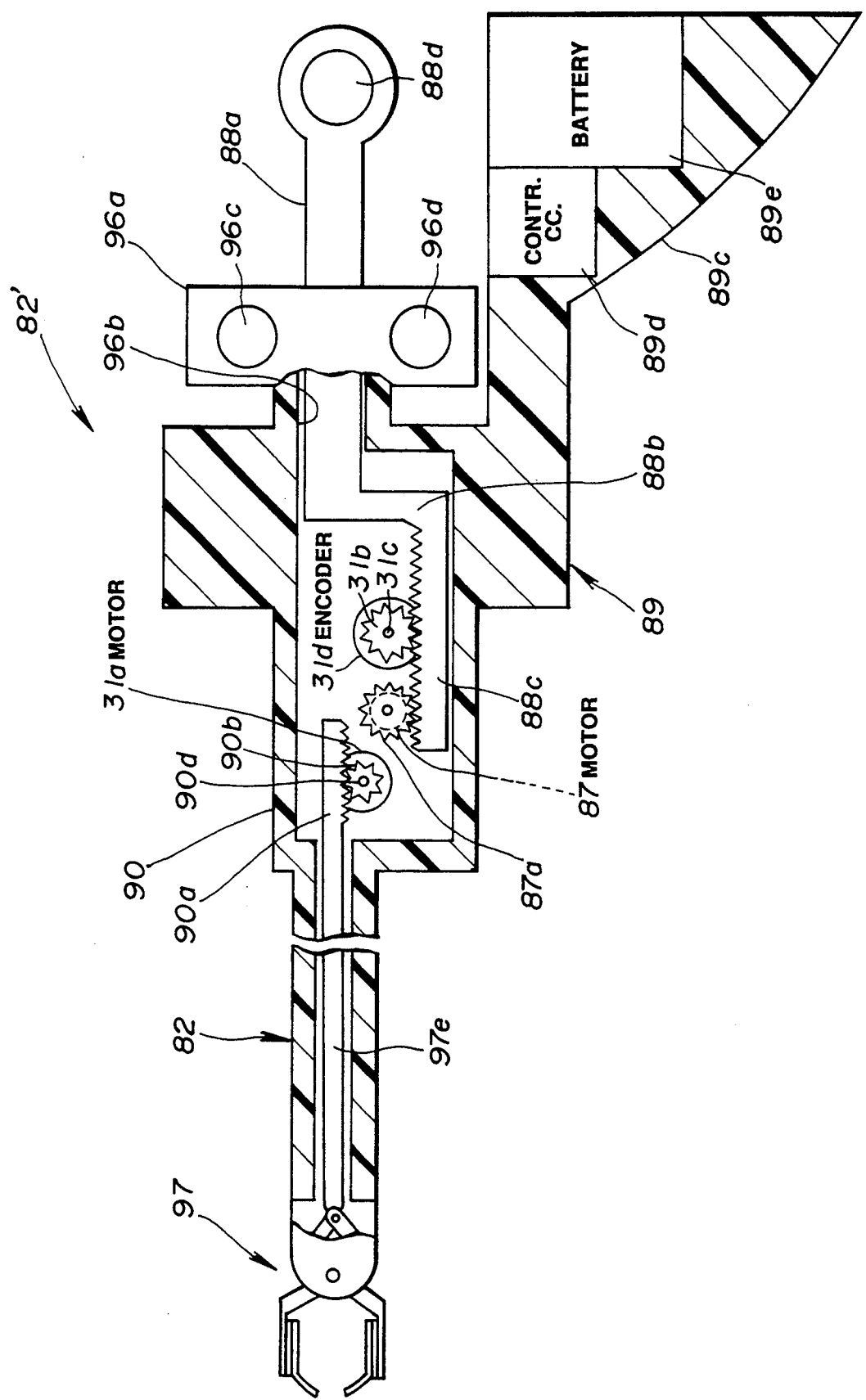

FIG. 9 shows a variant grasping forceps 82'. In the grasping forceps 82', an axis 90d on which a gear 90b is mounted to be engaged with a rack 90a in FIG. 4 is mounted on a rotation axis of a motor 31a. A moving rate of a flexible shaft 97e or an opening or closing rate of jaws 97a is controlled according to a rotating speed for the motor 31a.

An axis 31c on which a gear 31b is mounted to be engaged with a rack 88c in FIG. 4 is provided with a rotary encoder 31d. The rotary encoder 31d detects a manipulation rate of an operation knob 88a. The motor 31a is driven at a rate proportional to the detected manipulation rate.

In this variant, a tension detecting element 91 is not installed and a tension reproduction mechanism is not formed. This obviates a mechanism for sliding a slider 96a in the body 89a of an operation unit. The slider 96a is integrated to the body 89a of the operation unit. Leads are connected to a control circuit 89d without using contacts 90f and 89f.

Figure 10:
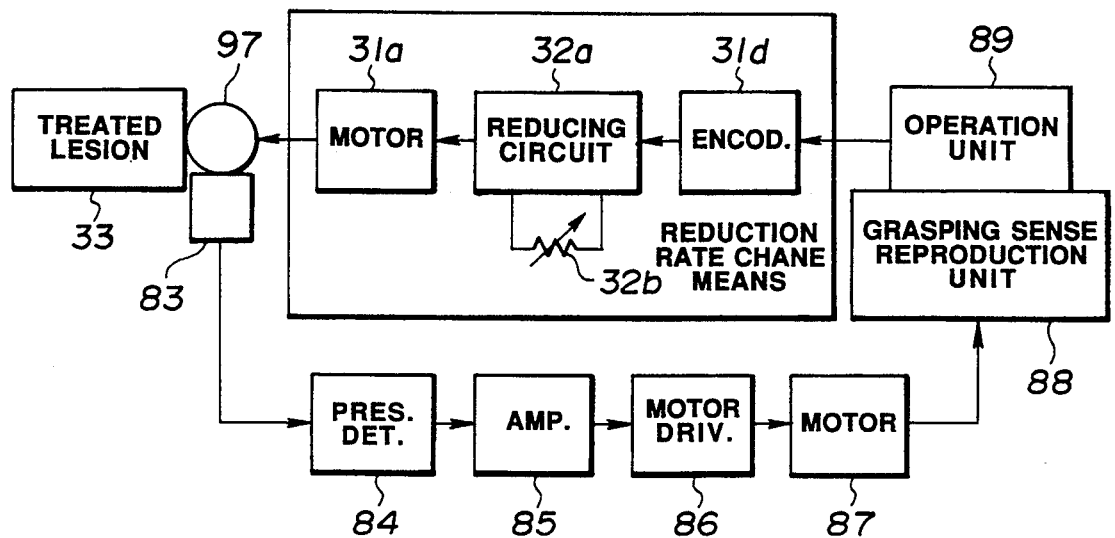

FIG. 10 shows the configuration of a control system of the grasping forceps 82'. An operation unit 89 is connected to a grasping section 97 serving as a treatment section via a conversion unit 32. The grasping section 97 grasps a treated lesion 33 for treatment.

The conversion unit 32 comprises a rotary encoder 31d for detecting a manipulation rate of an operation knob 88a, a reducing circuit 32a for reducing the manipulation rate the rotary encoder 31d detects, and a motor 31a to be driven with an output passing through the reducing circuit 32a.

The reducing circuit 32 is provided with a variable resistor 32b serving as a reduction factor change means for changing reduction factors. When the resistance of the variable resistor 32b varies, the level of a drive signal supplied to the motor 31a fluctuates. The level fluctuation changes the reduction factor at which an opening or closing rate of jaws 97a is reduced in association with a manipulation rate of the operation knob 88a.

As shown in FIG. 10, a grasping feeling reproduction unit 88 installed in an operation unit 89 is driven according to an output of grasping force detecting elements 83. A grasping force generated when a grasping section 97 grasps a tissue is detected by the grasping force detecting elements 83. According to the detected grasping force, an operation knob 88a is driven negatively to the manipulation for grasping. This drive allows a surgeon manipulating the operation knob 88a to tactilely perceive the grasping. The surgeon can perceive even elusive grasping or slight contact.

Numerals 83 and 88 in FIG. 10 represent the same components as those shown in FIG. 2. The description will be omitted. In FIG. 2, a mechanism corresponding to the conversion unit 32 is formed mechanically and not shown.

When a grasping section 97 grasps a treated lesion 33, the functions and advantages of this variant are identical to those of the previous embodiments. In this variant, when a variable resistor 32b is operated, an opening or closing rate of jaws 97a can be easily adjusted in association with a manipulation rate of an operation knob 88a. Therefore, the same control system can be employed for grasping forceps of different sizes. A surgeon can select a reduction factor as he/she likes.

In FIGS. 9 and 10, a grasping forceps is used for describing the embodiment. The embodiment, however, can apply to biopsy forceps and other treatment adapters.

Figure 11:
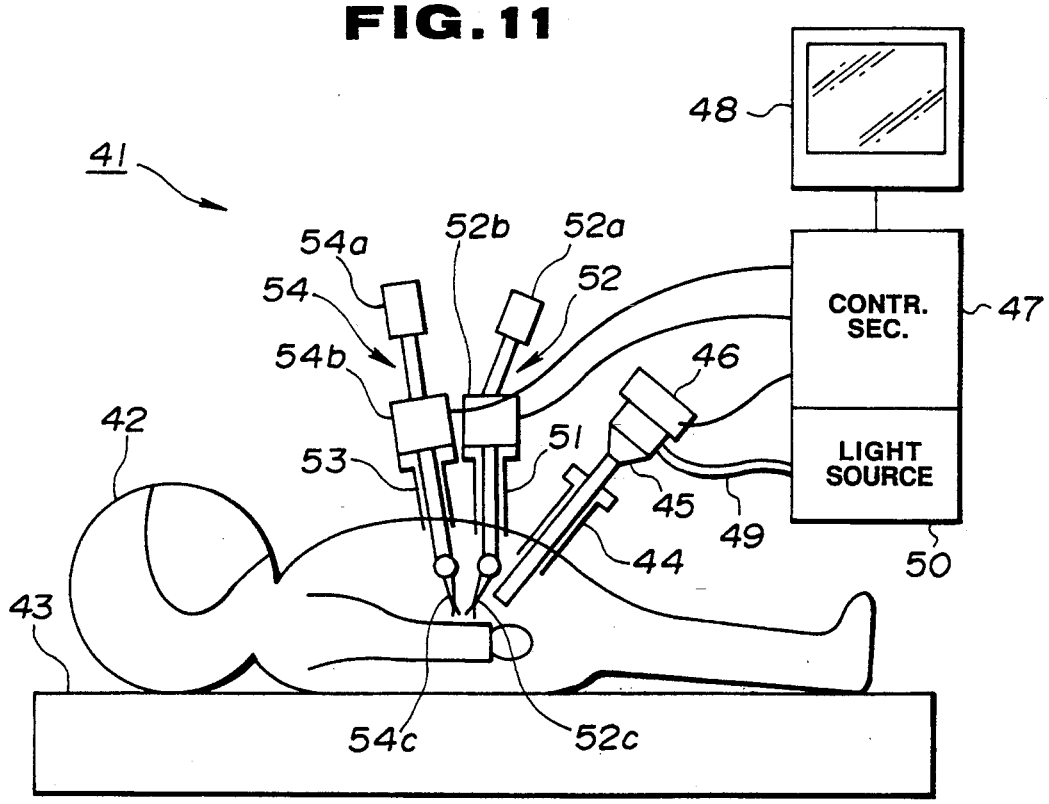
FIGS. 11 and 12 relate to the second embodiment of the present invention.

FIG. 11 shows a medical system 41 of the second embodiment of the present invention. The system 41 is designed for use in resecting, for example, a tissue of a lesion in an abdominal cavity under the endoscopic observation.

Holes for inserting equipment are formed in the abdominal cavity of a patient 42 lying in a bed 43 using a trocar which is not shown. A sheath 44 is inserted into a first hole. A rigid endoscope (laparoscope) 45 is inserted into the sheath 44. The laparoscope 45 is equipped with a TV camera 46. An image signal sent from an imaging means of the TV camera 46 is processed by a signal processing circuit in a control section 47. Then, the processed signal is displayed three-dimensionally on a TV monitor 48. The laparoscope 45 is connected to a light source 50 via a light guide cable 49. The light source 50 supplies illumination light.

A sheath 51 is inserted into a second hole. A grasping forceps 52 serving as a treatment adapter is inserted into the sheath 51. An operation unit 52a formed at the back of the grasping forceps 52 is manipulated to operate a grasping section 52c formed at the distal end via a conversion unit 52b. An actuator formed with, for example, a motor or a shape memory alloy, which is not shown, is placed in the conversion unit 52b. The grasping section 52c opens or closes, or moves in any three-dimensional direction in association with the manipulation of the operation unit 52a.

A manipulation rate of the operation unit 52a is reduced by the conversion unit 52b, then transmitted to the grasping section 52c. When the grasping section 52c is larger than the operation unit 52a, a manipulation rate of the operation unit 52a is amplified by the conversion unit 52b, then transmitted to the grasping section 52c.

Figure 12A:
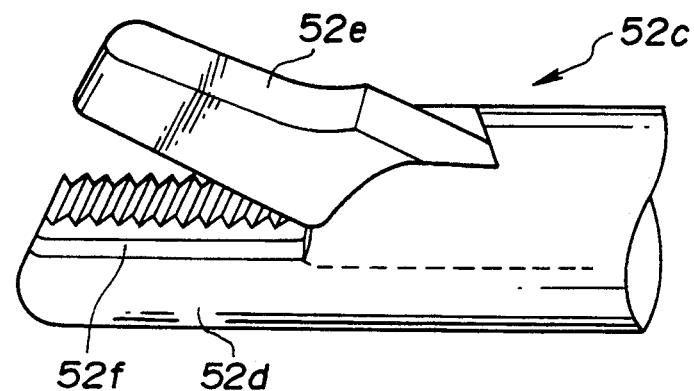
FIGS. 12(a) and (b) show the configurations of the distal portion of a treatment adapter used in this system.

In FIG. 12a, a state of contact when a grasping section 52c has grasped a tissue of a lesion is detected by a tactile sensor 52f installed in one of a stator grasping jaw 52a and a rotor grasping jaw 52e, which opens or closes against the stator grasping jaw 52d. The grasping jaws 52a and 52e form the grasping section 52c. The contact force detected by the tactile sensor 52f is transmitted to a control section 47 via a cable extending from a conversion unit 52b, then processed by a signal processing circuit in the control section 47. The signal processing feeds back a contact force negatively, so that the contact force will appear as a driving force for driving an actuator, which is not shown, installed in the conversion unit 52b or an operation unit 52a negatively to the manipulation for grasping. A surgeon manipulating the operation unit 52a assesses the degree of the fed-back driving force to tactilely perceive the degree of the contact force acting on the grasping section 52c and a tissue when the grasping section 52c gets in touch with the tissue.

The surgeon can view three-dimensional images displayed on a TV monitor 48 to visually understand the state of an operated region and the positional relationship between the operated region and the grasping section 52c. Thus, the surgeon can proceed with the surgical procedure with the backup of visual understanding.

Figure 12B:
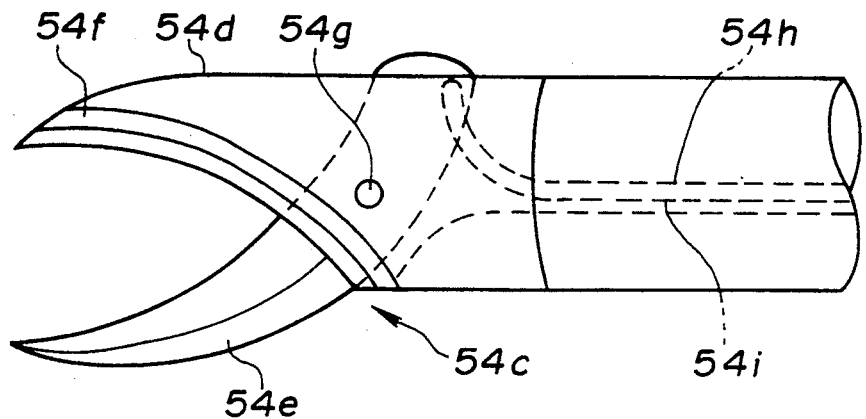

A sheath 53 is inserted into a third hole. A resection forceps 54 is inserted into the sheath 53. The resection forceps 54 includes an operation unit 54a, a conversion unit 54b, and a resecting section 54c. A state of contact when the resecting section 54c resects a tissue of a lesion is, as shown in FIG. 12b, detected by a tactile sensor 54f installed in, for example, a stator resecting jaw 54d forming the resecting section 54c. A rotor resecting jaw 54e swivels about a pivot 54g open or close against the stator resecting jaw 54d. When a wire 54h is advanced or withdrawn, the rotor resecting jaw 54e opens or closes. The tactile sensor 54f is connected to a signal line 54i. A contact force the tactile sensor 54f detects is transmitted to a control section 47 via a cable extending from the conversion unit 54b. Then, the output signal is processed by a signal processing circuit in the control section 47. This signal processing allows an actuator, which is not shown, to provide a driving force for driving an operation unit 54b negatively to the manipulation for resection. The operation unit 54a and conversion unit 54b have the same configurations as those for a grasping forceps 52.

The operation for manipulating the resecting forceps 54 is identical to that described for a grasping forceps 52.

In the above description, a state of contact between a grasping section 52c serving as a treatment section and a tissue is detected using a tactile sensor 52f or 54f. A means may be installed to monitor a fluctuation in current or voltage a driving power supply supplies to an actuator for driving the treatment section. Then, an output of the means may be fed back negatively, so that the output will negatively act on a force for manipulating an operation unit 52a or 54a. In the negative feedback, a larger contact force with which the treatment section touches the tissue results in a larger manipulation force required for providing a larger contact force. A surgeon feels a variation in manipulation force with his/her hand to recognize how the treatment section is working on the tissue.

Figure 13:
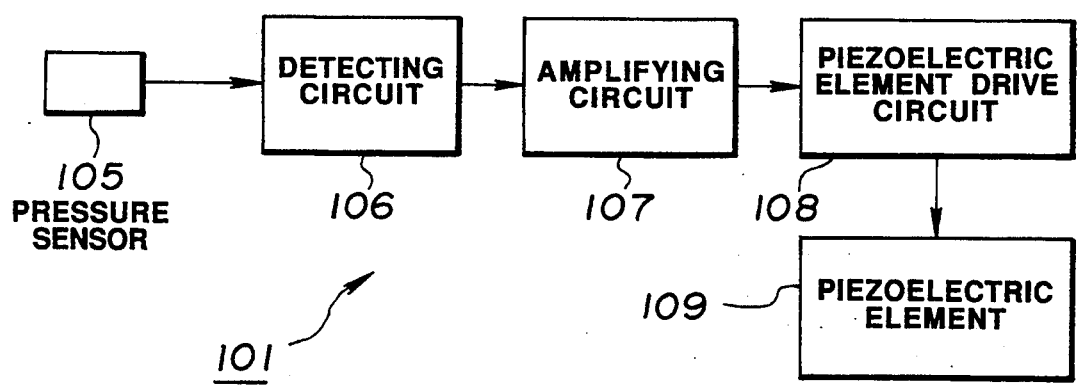

FIG. 13 shows a therapeutic apparatus 101 of the third embodiment of the present invention. The apparatus 101 notifies a surgeon of a feeling implying that a needle tip 103 of an injection needle 103 has punctured a tissue. As shown in FIG. 13, a pressure sensor 105 is interposed between the proximal end of the needle tip 103 of the injection needle 102 and the distal end of a syringe 104. A detecting circuit 106 assesses an output of the pressure sensor 105 to detect a pressure. Then, an amplifying circuit 107 amplifies the weak signal. With the amplified signal, a piezoelectric element drive circuit 108 drives a piezoelectric element 109 serving as a means for reproducing a feeling and eventually stretches the piezoelectric element 109.

A pressure sensor 105 senses puncture made with a needle tip, then provides a detecting circuit 109 with an output. Then, a piezoelectric element 109 installed on the back of a piston 110 of a syringe 102 is driven to stretch. The stretch (which causes a repulsive force to act on the finger placed on the back of the piston 110, and) notifies a surgeon of puncture. In this embodiment, circuits 111 including the detecting circuit 106 are incorporated in, for example, the back of the syringe 104. A contact 112 electrically couples the circuits 111 with the piezoelectric element 109 for signal transmission.

According to the third embodiment, puncture made with even a very small-diameter injection needle can be identified.

Figure 15:
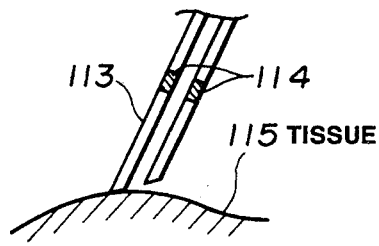

As shown in FIG. 15, a pressure sensor 114 may be incorporated in the middle of a needle tip 113 to sense the puncture or penetration onto a tissue 115 made with the needle tip. This will provide the same effects as the third embodiment.

Figure 16:
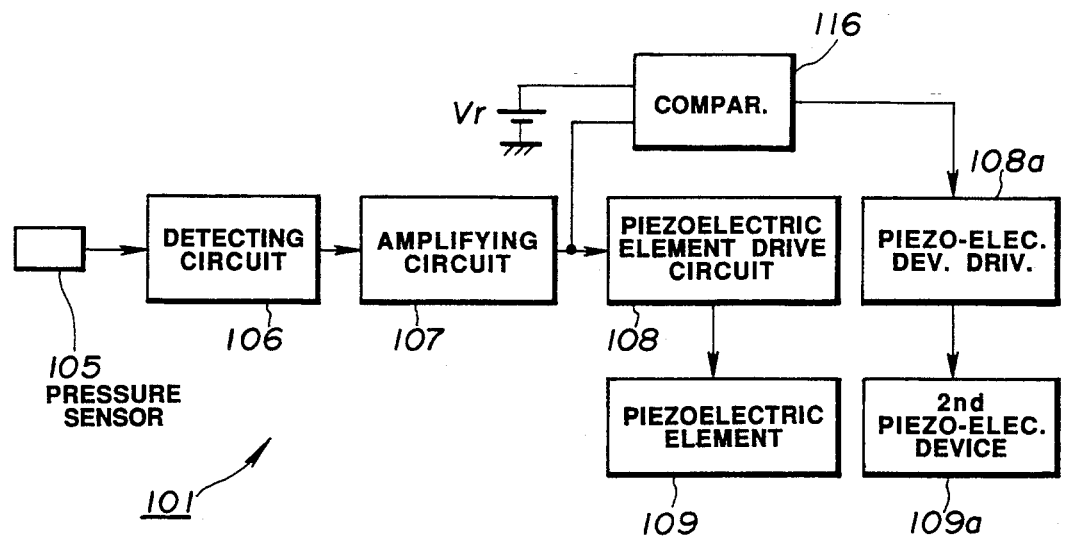

FIG. 16 shows a variant of a control system shown in FIG. 13. This variant further includes a restriction means for restricting a manipulation force for an operation unit. That is to say, an output of an amplifying circuit 107 shown in FIG. 13 is compared with a reference value Vr by a comparator 116. When the output of the amplifying circuit 107 exceeds the reference value Vr, the comparator 116 provides a second drive circuit 108a with a determination signal indicating that the output exceeds the reference value Vr. In response to the determination signal, the second drive circuit 108a outputs a drive signal for driving a second piezoelectric element 109a.

Figure 14:
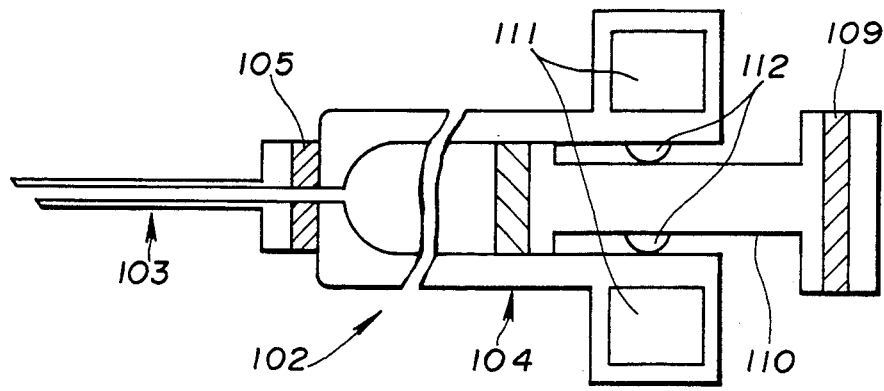

The second piezoelectric element 109a is formed, as shown in FIG. 17a, in a needle tip 103. With a drive signal sent from the second drive circuit 108a, the second piezoelectric element 109a contracts, for example, by d in the longitudinal direction of the needle tip 103. The contraction allows the apex of the needle tip 103 to retreat. Other components are identical to those shown in FIGS. 13 and 14.

The use of a syringe 101' further provides the advantages described below. As shown in FIG. 17a, assume that a first tissue 115a and a second stiffer tissue 115b reside side by side in the deep region of a tissue 115. When therapeutic fluid is to be administered to the first tissue 115a, if a needle tip penetrates through the tissue 115a and the apex of the needle tip reaches the second tissue 115b, a pressure sensor 105 provides a larger output. Then, a comparator 116 compares the output with a reference value Vr, then outputs a determination signal. Then, the drive signal sent from a second drive circuit 108a applies to a piezoelectric element 109a. As a result, the apex of the needle tip 103 retreats as shown in FIG. 17b. This may prevent puncture of the second tissue 115b or injection of therapeutic fluid into an incorrect tissue, improving or ensuring safety.

Next, various equipment having restriction means for improving or ensuring safety will be described.

FIG. 18 shows a treatment section of the distal portion of a laser probe in a therapeutic system of the fourth embodiment of the present invention.

Figure 19:
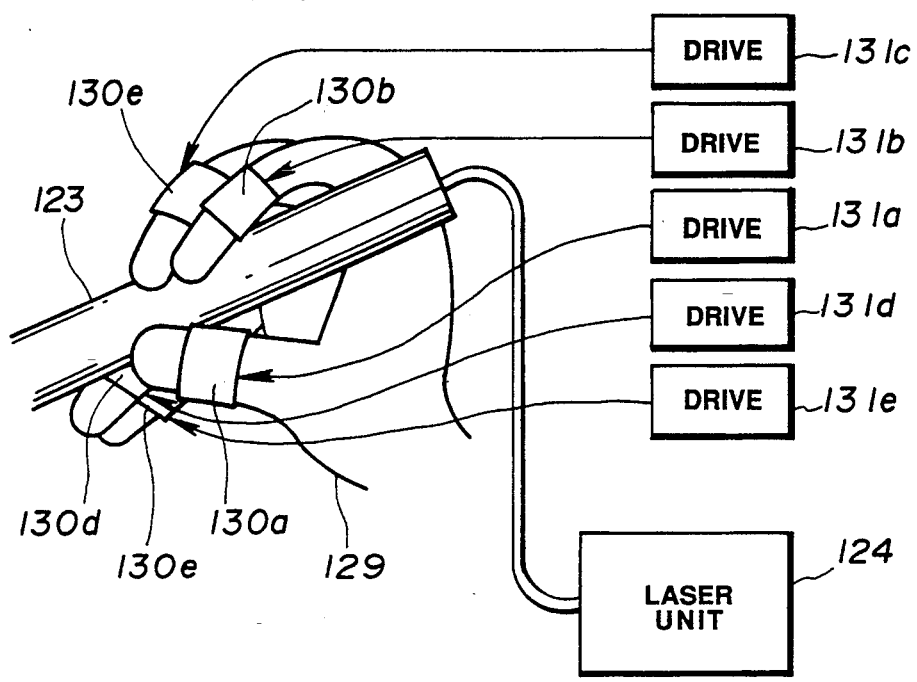

A laser probe 122 is routed through a protective sheath 123 as shown in FIG. 18, then connected to a laser 124 via a guide cable extending from the back of the laser probe 122 as shown in FIG. 19. A laser beam coming from the laser 124 is emitted from the distal portion of the laser probe 122 to cauterize the accreted region of the liver and cholecyst.

Pressure sensors 125u, 125d, 125l, and 125r (125l is not shown) are installed inside the tip of the sheath 123 to detect whether the contact direction of the tip of the laser probe 122 is up, down, left, or right. A strain gauge 121 is installed to detect a pressure working when the laser probe 122 is placed on a tissue.

Figure 20:
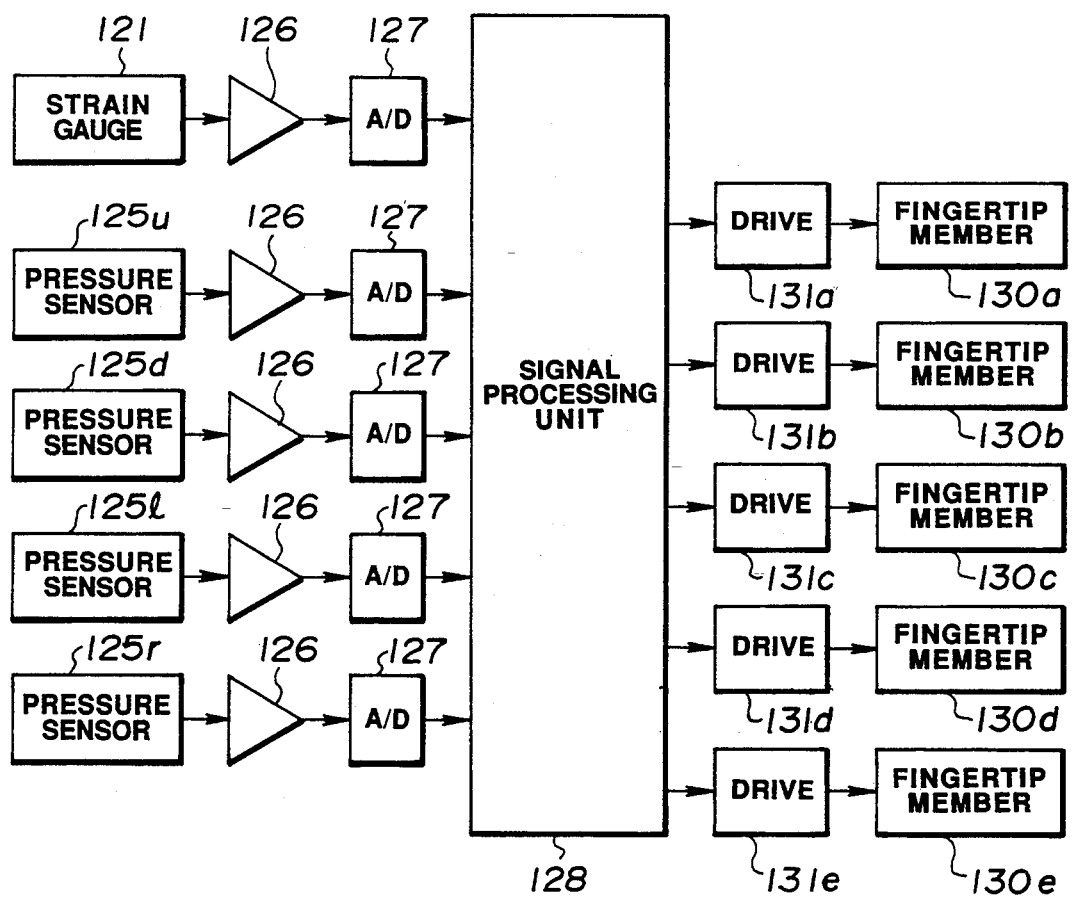

As shown in FIG. 20, the outputs of the strain gauge 121 and pressure sensors 125i (i=u, d, l, and r) are amplified by amplifiers 126, then converted into digital signals by A/D converters. The digital signals are supplied to a signal processing unit 128. The signal processing unit 128 performs signal processing to control the movements of fingertip members 130a, 130b, 130c, 130d, and 130e put on the thumb, index finger, middle finger, ring finger, and little finger of a surgeon's hand 129 as shown in FIG. 19, then generates drive signals for driving the fingertip members 130a, 130b, 130c, 130d, and 130e using fingertip member drives 131a to 131e.

The fingertip members 130a to 130e are put on the fingertips of a surgeon's hand 129 holding the sheath 123, and the movements are controlled by the fingertip member drives 131a to 131e. Each of the fingertip member drives 131a to 131e is made up of a gear and a motor.

In this embodiment, an output of a strain gauge 121 is assessed to detect a pressure acting when a laser probe 122 is in contact with a tissue. The pressure is reproduced in fingertips to be moved by driving fingertip members 130a to 130e. Then, pressure sensors 125i are used to control the movements of the fingertip members 130a to 130e so as not to resect the cholecyst. In the state shown in FIG. 18, when the cholecyst bordered on the liver is resected to dissolve accretion, the cholecyst may rupture to leak bile to the abdominal cavity. Generally, the liver is resected. During resection, if the tip of the laser probe 122 touches the cholecyst, the pressure sensors 125i detect the fact, and restrict the movements of the fingertip members 130a to 130e so that the fingers will move to separate the laser probe 122 from the cholecyst.

Thus, the cholecyst can be prevented from being cauterized accidentally.

The fingertip members 130a to 130e are provided with sensors, which are not shown, for detecting the movements of fingers. Output signals of the sensors are processed by a signal processing unit which is not shown. Thus, the distal portion of a laser probe 122 moves according to the movements of the fingers.

Figure 21:
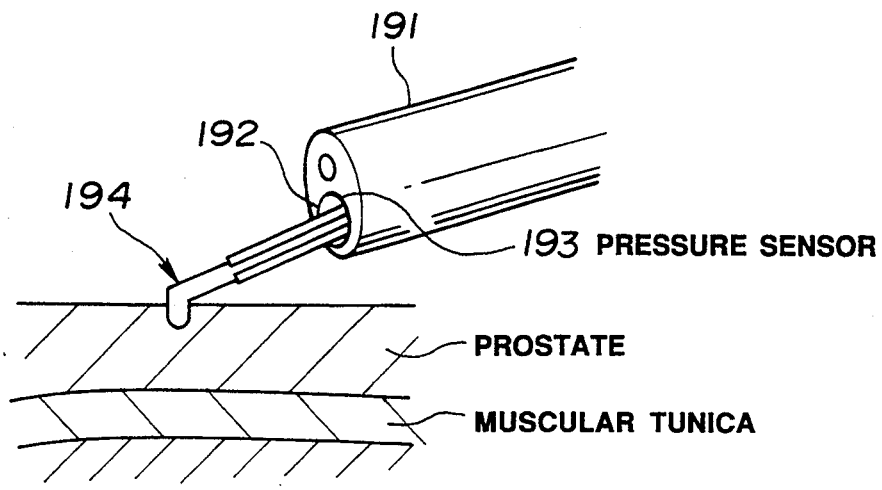

FIG. 21 shows resection of a prostate using a diathermic probe 194 for a therapeutic apparatus of the fourth embodiment of the present invention. Herein, a pressure sensor 193 is installed in a channel 192 of an endoscope 191. The pressure sensor 193 is installed in the distal portion of the channel 192. The pressure sensor 193 detects, for example, the stiffness of a tissue including the prostate in contact with the resecting section of the tip of the diathermic probe 194 inserted into the channel 192, then uses a detected signal to control the movements of fingertip members as described in the fourth embodiment.

For example, while a prostate is being resected, if a resecting section reaches the muscular tunica inferior (internal) to the prostate, a pressure sensor 193 detects the change in stiffness between the prostate and muscular tunica. Then, the movements of fingertip members put on a surgeon's fingers are controlled so that a diathermic probe 194 will part from the muscular tunica. Pressure sensors may be used on behalf of fingertip member drives to transmit pressures to fingers.

Figure 22:
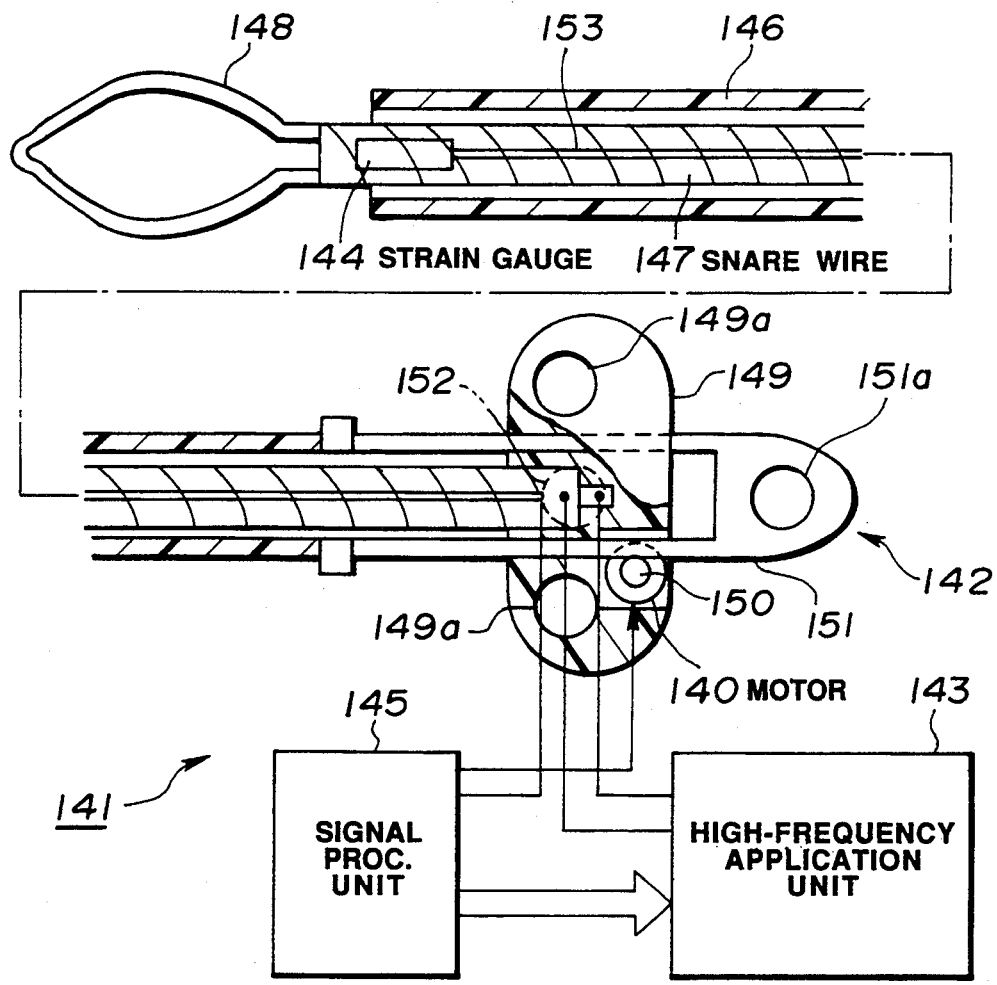
FIGS. 22 to 25 relate to the fifth embodiment of the present invention.

FIG. 22 shows an intelligent diathermic treatment apparatus 141 of the fifth embodiment of the present invention. The diathermic treatment apparatus 141 comprises a diathermic snare 142 for resecting a lesion with high-frequency current, a high-frequency supplier 143 for supplying high-frequency current to the diathermic snare 142 for resection, a strain gauge 144 mounted on the diathermic snare to detect a pull, a signal processing unit 145 for performing signal processing to control the operation of the high-frequency supplier 143, and a drive motor 140 for outputting a driving force to a slider 149 in an operation unit which activates resection with an output from the signal processing unit 145.

In the diathermic snare 142, a snare wire 147 is running through a hollow tube sheath 146. The tip of the snare wire 147 is connected to a resection snare 148 which functions as a resecting section. The back of the snare wire 147 is connected to a slider 149 for activating resection. The back of the tube sheath 146 is connected to a handle body 151. The handle body 151 and slider 149 are provided with finger holes 151a and 149a. With fingers inserted into the finger holes 151a and 149a, the slider 149 can be moved back and forth on the handle body 151 so that the resection snare 148 will project beyond the tip of the tube sheath 146 or move backward to lie in the opening of the tube sheath 146.

Figure 23:
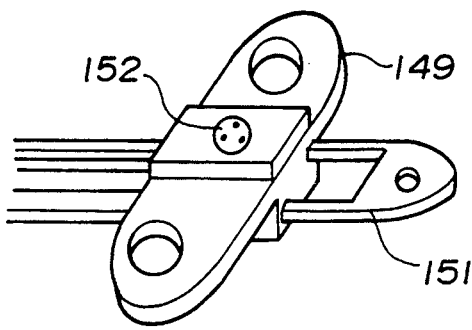

The slider 149 is provided with a plug 152 as shown in FIG. 23. The snare wire 147 is connected to a high-frequency supplier 143 via two contacts of the plug 152, and thereby supplies high-frequency current to the snare 148.

A strain gauge 144 is adhered near the tip of the snare wire 147 or in the vicinity of the resecting snare 148. An output signal of the strain gauge 144 travels over a signal line 153 running through the snare wire 147 to reach a plug 152 of a slider 149. The plug 152 connects the output signal to the signal processing unit 145.

Figure 24:
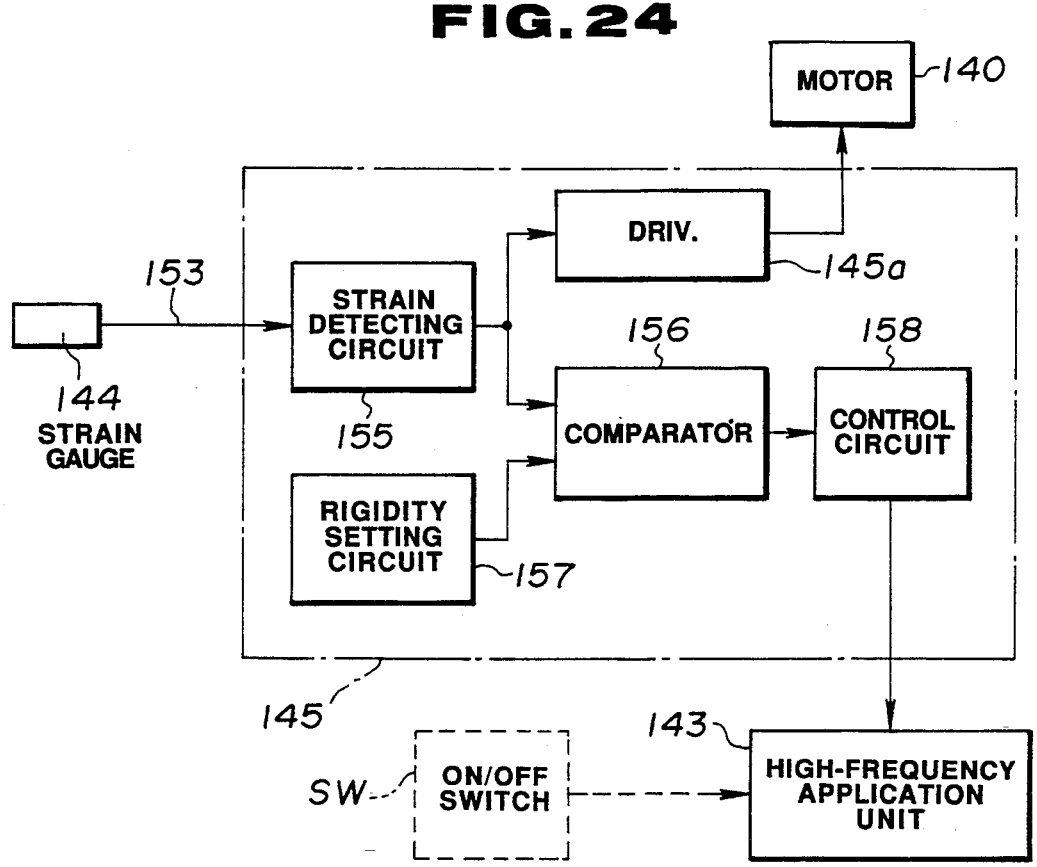

FIG. 24 shows the configuration of the signal processing unit 145. An output signal of a strain gauge 144 enters a strain detecting circuit 155 to be amplified. Then, the amplified signal goes to a drive circuit 145a and a comparator 156. The drive circuit 145a amplifies current to drive a motor 140 for providing a slider 149 with a moving force. Specifically, the strain gauge 144 deforms according to a contact force working when a resecting snare 148 touches a tissue, then a signal proportional to the force is supplied to the motor via the drive circuit 145. Therefore, the motor 140 is driven with a drive signal of a current value proportional to a contact force. The rotation force of the motor 140 acts as a moving force on the slider 149 movable on a handle body 151. (In this embodiment, the motor 140 is incorporated in the slider 149, and applies a moving force to the side of the handle body 151 pressing a roller 150.) The moving force is proportional to the contact force the strain gauge 144 detects and withdraws the resecting snare 148. The moving force allows a surgeon to tactilely perceive the state of contact.

An output of a comparator 156 is compared with an output signal of a stiffness setting circuit 157 for setting a level at which make is disabled. The output of the comparator 156 is fed to a high-frequency supplier 143 via a control circuit 158 to control make/break of the high-frequency supplier.

For example, an output detected on a strain gauge 144 exceeds a level specified in a stiffness setting circuit 157, an output of a comparator 156 causes a control circuit 158 to output a stop signal for breaking a high-frequency supplier 145 to cut off high-frequency current (disabling electric conduction) supplied to a diathermic snare 142.

According to this embodiment, a grasping force of the diathermic snare 142 is assessed to detect stiffness of a resected region and restrict a range of resection. This prevents resection of a region that should not be resected; such as, the muscular tunica. FIG. 25 is an explanatory diagram showing the restricted resection.

Figure 25A:
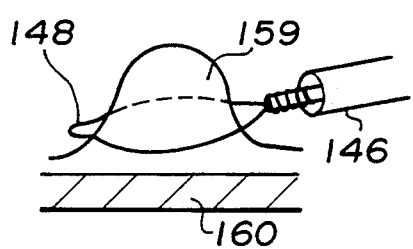
FIGS. 25(a) and (b) are explanatory diagrams of the operation of the fifth embodiment.
Figure 25B:
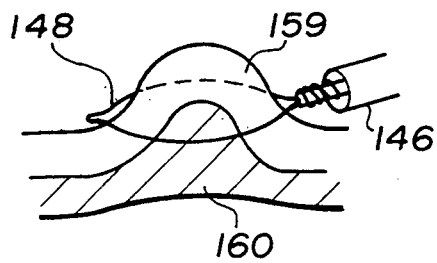

As shown in FIG. 25a, if a tumor at which a resecting snare 148 lies contains only the mucosal layer of tympanic membrane 159 (or submucosal layer or chorionic membrane), it is soft. Therefore, even when a slider 149 is pushed, a strain gauge 144 provides a small output.

In FIG. 25a, the muscular tunica underlies the mucosal layer of tympanic membrane 159. On the other hand, in FIG. 25b, even the muscular tunica is caught by the snare 148. In this case, when the snare 148 resects the mucosal layer of tympanic membrane 159 and reaches the underlying muscular tunica 160, since the muscular tunica 160 is stiff, a larger force needs to push the slider 149. This causes the strain gauge 144 to provide a larger output. A signal processing unit 145 identifies this output variation, then outputs a stop signal to a high-frequency supplier 143 to stop making high-frequency current.

According to this embodiment, the muscular tunica 160 is prevented from being resected.

In this embodiment, an output signal of a strain gauge 144 is used to control make of a high-frequency supplier 143. As indicated with a dashed line in FIG. 24, a switch for turning on or off make/break control may be installed to selectively specify make control at an surgeon's option.

Figure 26:
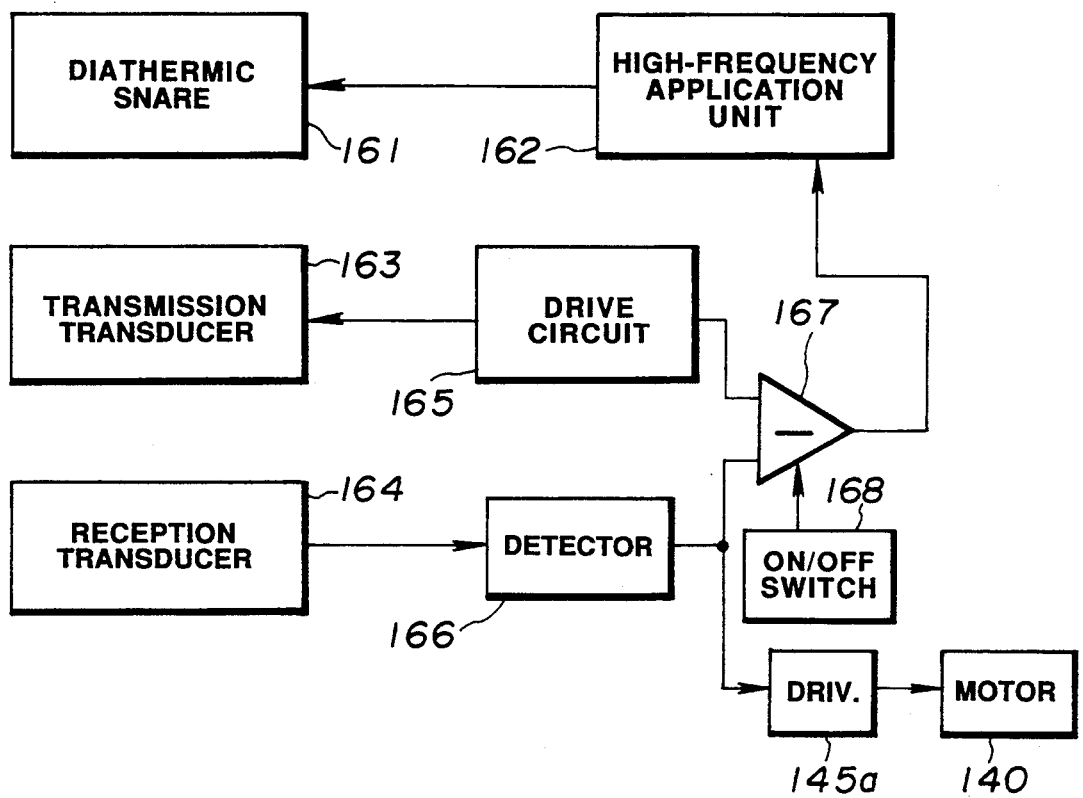
FIGS. 26 to 28 relate to the sixth embodiment.

FIG. 26 is a block diagram showing the configuration of the sixth embodiment of the present invention. This embodiment includes a diathermic snare 161, a high-frequency supplier 162 for supplying high-frequency current to the diathermic snare 161, transmission and reception (ultrasonic) transducers 163 and 164 designed to control high-frequency supply, a drive circuit 165 for driving the transmission transducer 163, a detector 166 for processing signals the reception transducer 164 receives, and a comparator 167 for comparing the outputs of the drive circuit 165 and detector 166. The output of the comparator 167 is assessed to control make/break of the high-frequency supplier 162. With the output of the detector 166, a motor 140 installed in an operation unit is driven by a drive circuit 145a.

Make/break control of the high-frequency supplier 162 can be selectively actuated using an ON/OFF switch 168.

Figure 27:
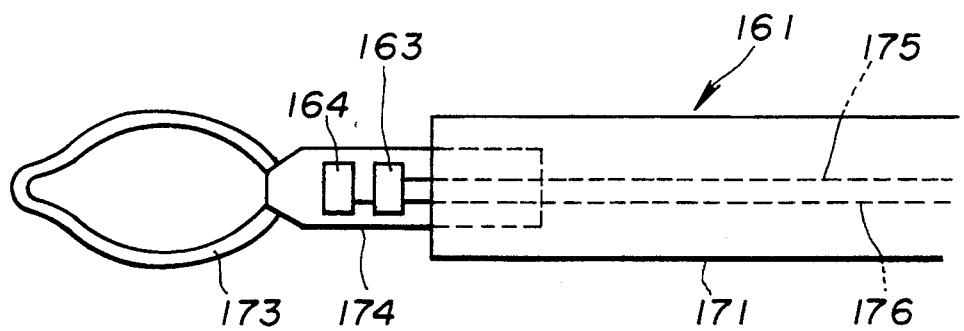
Figure 28:
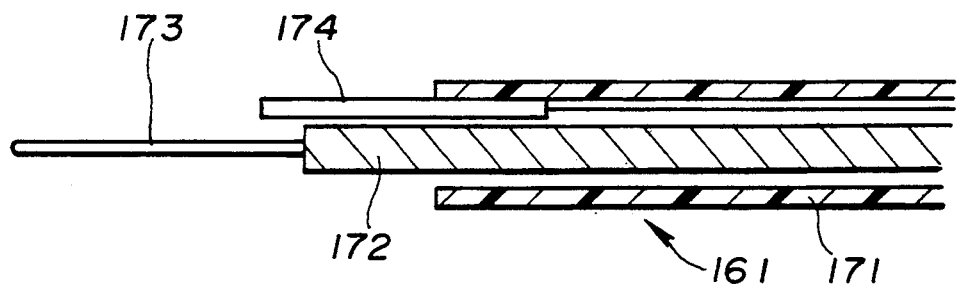

FIGS. 27 and 28 show the configuration of the distal portion of a diathermic snare 161. A snare wire 172 is running through a tube sheath 171. A loop-shaped resection snare 173 is formed at the tip of the snare wire 172. A sensor unit 174 made up of a transmission transducer 163 and a reception transducer 164 is mounted inside the tip of the tube sheath 171. The transmission transducer 163 and reception transducer 164 are connected to a drive circuit 165 and a detector 166 via signal lines 175 and 176.

In this embodiment, a transmission transducer 163 emits ultrasound with a certain frequency fo to a subject to vibrates the subject. On the other hand, a reception transducer 164 detects ultrasound with a frequency fx in real time. A comparator 167 compares the frequencies fo and fx to detect the stiffness of the subject. For example, assume that a sensor unit 174 is pressed to a subject with a certain contact pressure. If the subject is stiff, the contact area becomes small. The frequency variation results from the stiffness effect of the subject. When the subject is soft, the contact area is large. This results in a mass effect. Thus, by calculating a frequency variation, whether a subject is stiff or soft can be detected in real time. A subject drives a motor 140 via a drive circuit 145a.

When identifying a frequency exceeding a certain value and determining stiffness, the comparator 167 outputs a stop signal to the high-frequency supplier 162 (when the ON/OFF switch 168 is on. If the ON/OFF switch 168 is off, the stop signal is not transmitted).

The operation and effects of this embodiment are almost identical to those of the fifth embodiment. According to this embodiment, stiffness of a deep region can be detected.

Figure 29:
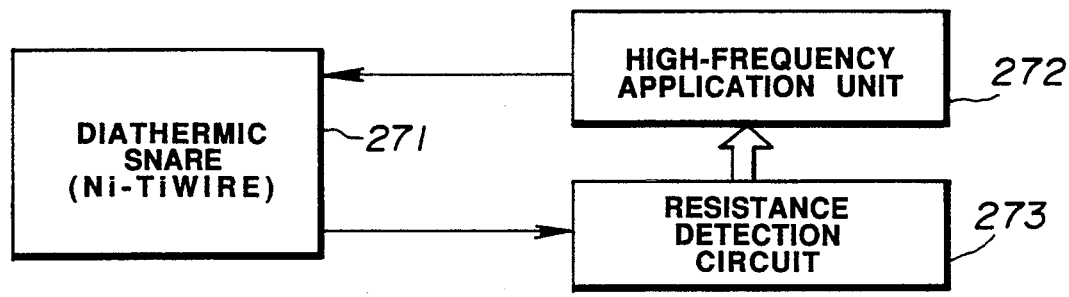
FIGS. 29 to 31 relate to the seventh embodiment of the present invention.

FIG. 29 shows the configuration of a control system for making or breaking high-frequency current in the seventh embodiment. This embodiment includes a diathermic snare 271 made of a super elastic alloy, a high-frequency supplier 272, and a resistance detector 273 for detecting a resistance of the diathermic snare 271. A wire made of Ni-Ti or other super elastic alloy is employed for at least either a snare wire or a snare of the diathermic snare 271. The super elastic alloy has a characteristic that the resistance gets higher with a stress in a super elastic region.

Figure 30:
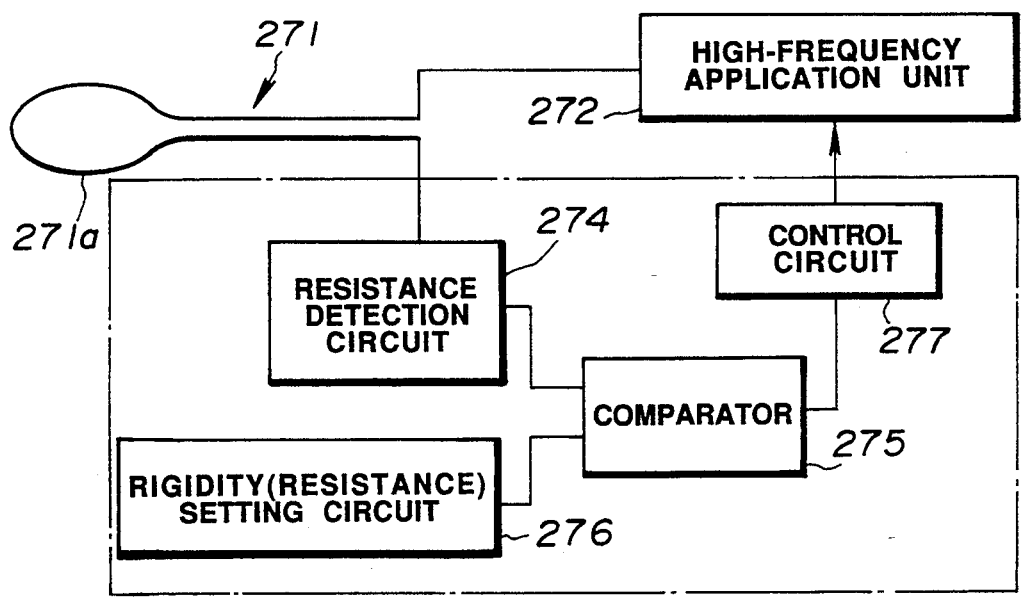

In this embodiment, a resistance detector 273 detects a resistance of a diathermic snare 271. When the resistance detector 273 detects a resistance exceeding a certain value, it determines that the muscular tunica is caught. Then, the resistance detector 273 outputs a high-frequency stop signal to a high-frequency supplier 272 to stop mixing. FIG. 30 shows the specific configuration of the resistance detector 273.

A diathermic snare 271 is connected to a high-frequency supplier 272 and to a resistance detecting circuit 274. For example, a resistance of a snare wire including a resecting snare 271a made of, for example, a Ni-Ti wire is detected and supplied to one input terminal of a comparator 275. The other input terminal of the comparator 275 is provided with a reference value a stiffness (resistance) setting circuit 276 specifies. When the comparator 275 detects a resistance exceeding the reference value, it outputs a detection signal to a control circuit 277. In response to the detection signal, the control circuit 277 outputs a stop signal to the high-frequency supplier 272. Also included is a means for reproducing a state of contact of the resecting snare 271a, which is not shown.

The operation and effects of this embodiment are almost identical to those of the sixth embodiment. Another advantage is that a small-diameter insertion tube can be realized because a diathermic snare 71 itself serves as a sensor.

Figure 31:
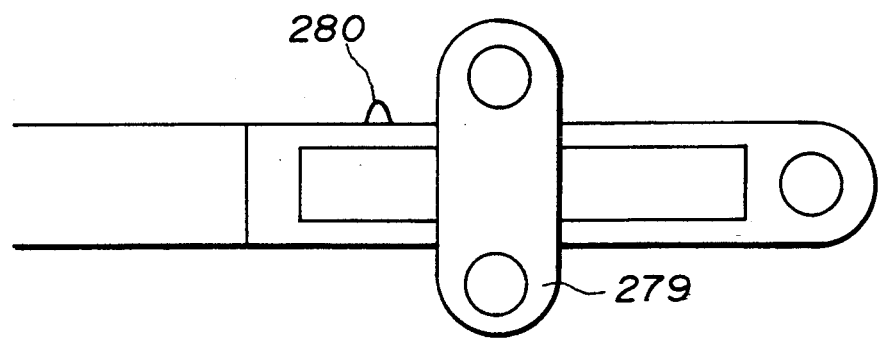

FIG. 31 shows the proximal portion of a diathermic snare in a variant of the seventh embodiment. In this variant, when a resistance detector 273 shown in FIG. 29 or 30 identifies a resistance exceeding a predetermined value, the resistance detector 273 outputs a make signal to a stopper 280 made of a shape memory alloy (hereafter, SMA) installed in the middle of a movable range of a slider 279. Then, the stopper 280 protrudes. The protruded stopper 280 disables the slider 279 to slide, thus preventing the muscular tunica from being resected.

In this variant, the high-frequency supplier 272 need not stop outputting making current. Alternatively, the movement of an operation unit may be restricted at a lower level than a level for stopping making current, or make/break may be disabled at a higher level.

The scope of this variant is not limited to the seventh embodiment, but may apply to, for example, the fifth and sixth embodiments. A stiffness detection signal may be used to actuate the SMA stopper 280. The variant is not restricted to a diathermic snare but will prove effective for use in a biopsy forceps and other treatment adapters.

According to the aforesaid embodiment, even a treatment adapter employing a remote control or a motor can be operated with the same hand feeling as that given when the treatment adapter is operated directly with the hand. Delicate treatment can be proceeded with a hand feeling similar to that given when non-delicate treatment is done, because a force actually required for the treatment is amplified and returned. When a treatment adapter is inserted into a channel of an endoscope, the treatment adapter can be operated effortlessly with realization of an environment (operating circumstances) ensuring the same hand feeling as that given by operating the distal portion of the treatment adapter directly with a hand.

When a treatment apparatus of, for example, the first embodiment is used with it inserted into a channel of an endoscope, the operation of a treatment section in the distal portion, which is associated with the manipulation of the treatment apparatus, can be reproduced in an operation unit at a surgeon's hand. On the other hand, the incorporation of a means for ensuring safety is expected in case that the distal portion of an endoscope may hit a wall of a body cavity during bending. An endoscope system having the means will be described in conjunction with FIG. 32.

Figure 32:
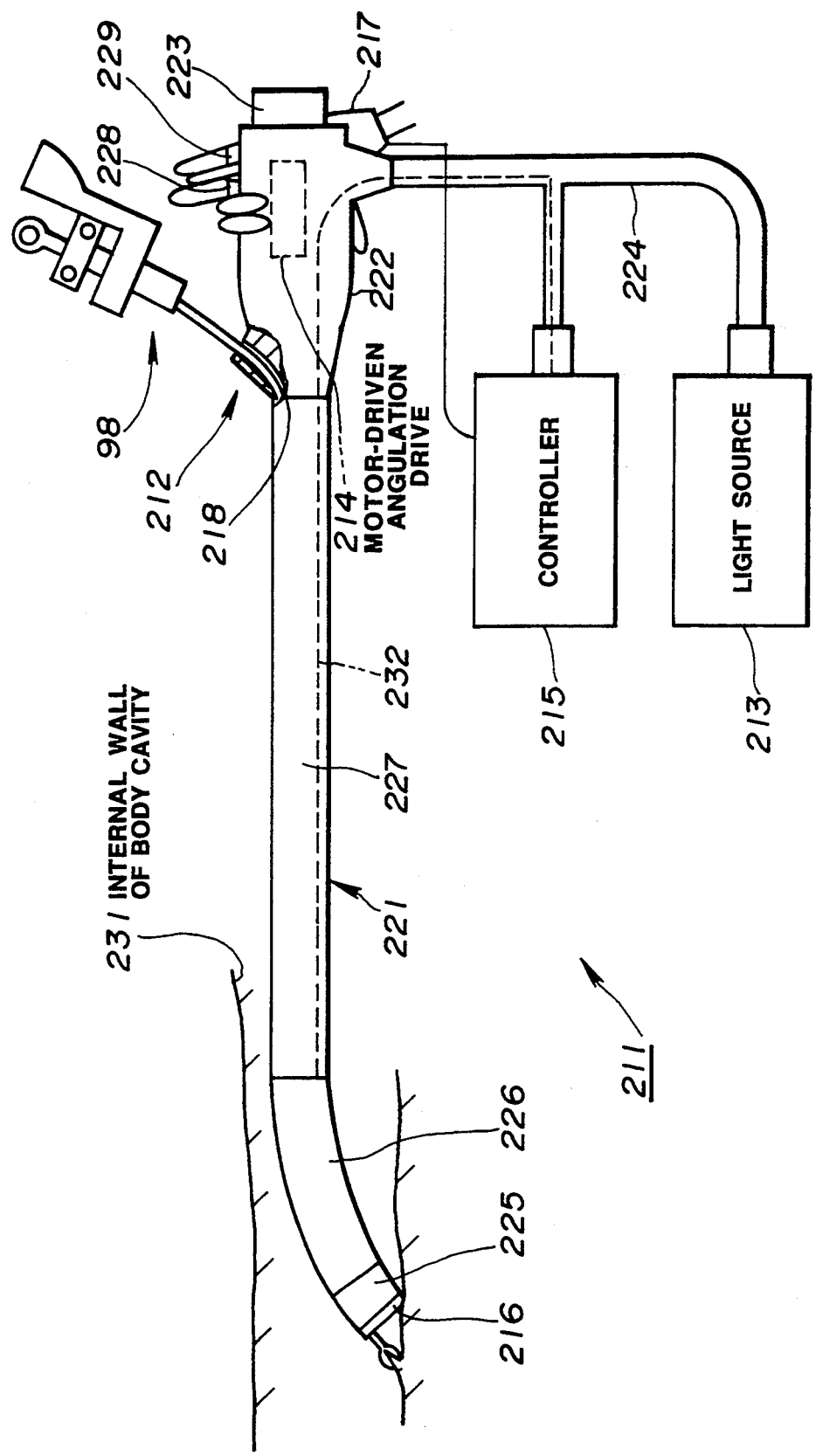
FIGS. 32 to 34 relate to the eighth embodiment.
Figure 33:
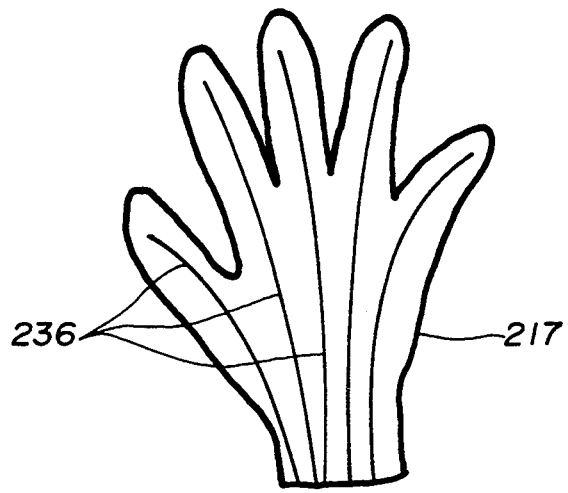
Figure 34:
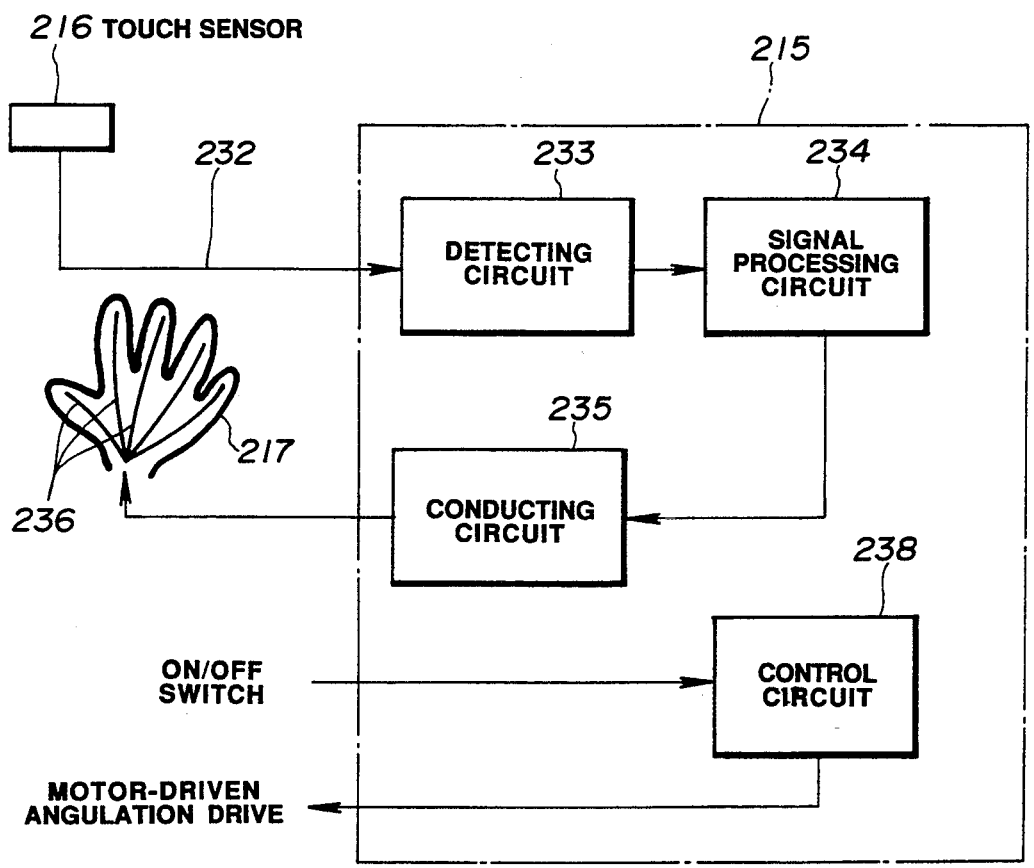

An endoscope system 211 of the eighth embodiment shown in FIG. 32 comprises a motor-driven angulation endoscope 212, a light source 213 for supplying illumination light to the endoscope 212, a control 215 for controlling a motor-driven angulation drive 214 of the endoscope 212, a touch sensor 216 for transmitting a detection signal to the control 215, a glove whose operation is controlled with an output signal of the touch sensor 216 which is processed by the control 215, and a biopsy forceps 98 of, for example, FIG. 7 serving as a treatment adapter to be inserted into a channel 218 of the endoscope 212.

The endoscope 212 comprises an elongated insertion tube 221 having flexibility, a large-diameter operation unit 222 coupled to the back of the insertion tube 221, an eyepiece unit 223 formed on the top of the operation unit 222, and a cable 224 extending from the side of the operation unit 222. The cable 224 bifurcates intermediately. The connectors can be connected to the control 215 and to the light source 213.

In the insertion tube 221, a rigid distal end 225 is formed in the distal portion, a bending section 226 is adjoining the distal end, and a flexible section 227 is extending from the back of the bending section 226 to the front of the operation unit 222. A ring-shaped touch sensor 216 is mounted on the front of the distal end 225 of the insertion tube 221. Motor-driven angulation buttons 228 and 229 are installed on the side of the operation unit 222. When the buttons 228 and 229 are pressed, the bending section 226 bends vertically or laterally.

The light source 213 supplies illumination light to the end surface on the side of a surgeon's hand of a light guide running through the endoscope. The light guide is not illustrated. The illumination light travels along the light guide, then comes out from other end surface on the side of the distal end 25. The illumination light illuminates an internal wall of a body cavity or a subject into which the insertion tube is inserted.

An image of the illuminated internal wall is formed on the focal plane in the distal end 225 by means of an objective which is not shown. On the focal plane, one end surface of an image guide (not shown) is arranged. The image guide transmits an optical image to the end surface of an eyepiece unit 23. Then, the optical image can be observed through an eyepiece in the eyepiece unit 23 in an enlarged scale.

When the distal end 225 touches the internal wall of the body cavity 231, a touch sensor 216 mounted on the distal end 225 outputs a detection signal according to the degree of contact or a resistance variation. The detection signal is transmitted to a control 215 over a signal line 232 running through an insertion tube 221. After leaving the control 214, the detection signal goes to a detecting circuit 233. Then, contact is detected by checking if a resistance variation or a voltage fluctuation exceeds a certain threshold.

The output of the detecting circuit 233 is supplied to a signal processing circuit 234. The signal processing circuit 234 performs signal processing to drive a glove 217. Then, an output of the signal processing circuit 234 passes through a conduction circuit 235 to drive SMAs 236 in the glove 217. In the glove 217, the SMAs 236 run along the routes of inserting fingers into the glove 217. The SMAs 236 are stretching in an nonconducting state in which no current is supplied from the conduction circuit 235. In this state, the glove 217 can be bent effortlessly. Specifically, fingers can be put into the glove 217 to grip an operation unit 222 as shown in FIG. 32. Then, motor-driven angulation buttons 228 and 229 can be pressed.

On the other hand, when the conducting circuit supplies current to the SMAs 236, the SMAs 236 enter a conducting state. Then, the SMAs 236 are heated to contract. In this state, when, for example, fingers have been bent inward to press the buttons 228 and 229, a force works to stretch the fingers and to weaken the force of pushing down the buttons 228 and 229.

When the button 228 or 229 is pressed, a control circuit 238 detects the on or off state. Depending on the detected on or off state, the control circuit 238 drives a motor-driven angulation drive 214 to bend a bending section 226 vertically or laterally.

According to the eighth embodiment, a touch sensor 216 detects if a distal end 25 touches an internal wall of a body cavity. When the distal end 25 touches the internal wall of a body cavity, a conduction circuit 235 flows current through SMAs 236 in a glove 217 to heat the SMAs 236. Then, a surgeon is provided with a feedback to become aware that the distal end 225 has touched the internal wall of the body cavity. Moreover, the surgeon is forced to weaken the force of pressing buttons 228 and 229, so that he/she cannot continue bending. Thus, safety is ensured.

Thus, according to the eighth embodiment, when a hand is put into a glove 217, even if the distal portion of an insertion tube bends during insertion and touches an internal wall of a body cavity 231, the contact is fed back to a surgeon. Therefore, the surgeon can be aware of the contact. Moreover, since a force works to discourage bending, even if a hazardous attempt is made to further bend the distal end of the insertion tube, it fails. Thus, the internal wall of the body cavity 231 will not be injured or holed.

Next, an embodiment of an intraoperative microscope permitting improved operability will be described.

Intraoperative microscopes permitting surgery under microscopic observation realize precise operations. Ideal functioning of an intraoperative microscope is that the intraoperative microscope allows a surgeon to proceed in a surgical procedure without distracting his/her visual line. A foot switch has been used to control an intraoperative microscope in the past.

However, the sophistication of surgery has resulted in an increased number of manipulations to be performed at an operation unit. The foot switch cannot afford to control all the manipulations or at least cannot pass delicate control. This embodiment resolves these problems.

Figure 36:
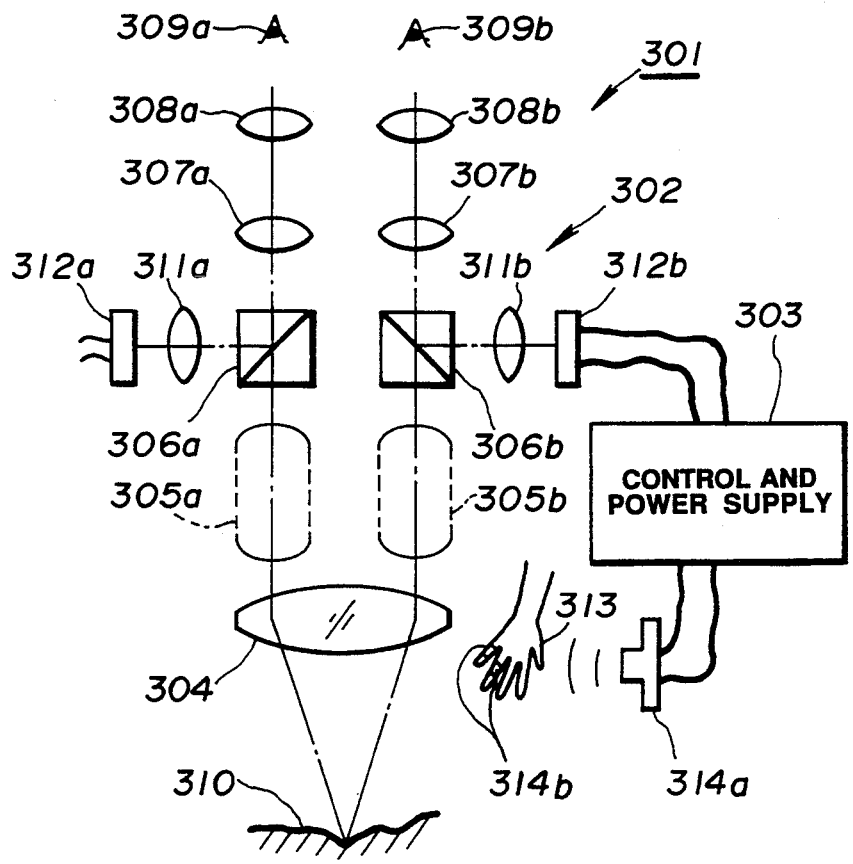

An intraoperative microscope 301 of the ninth embodiment shown in FIG. 36 comprises a main unit 302 of the intraoperative microscope, and a control and power supply 303 made up of a control means for driving or controlling the main unit 302 of the intraoperative microscope and a power supply means for supplying power to actuate the control means.

Figure 38:
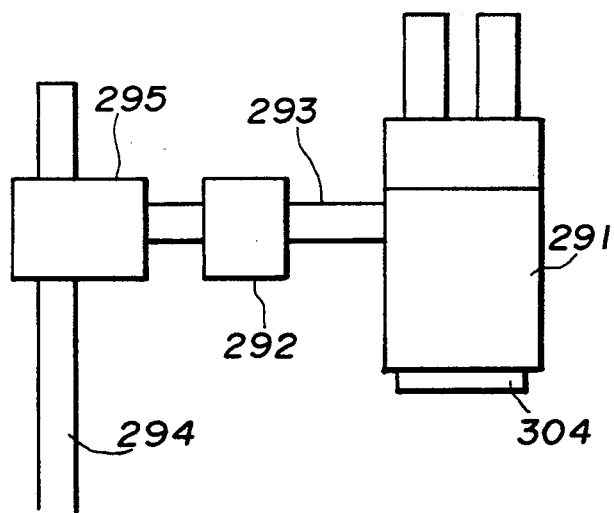

FIG. 38 shows an optical system for a main unit 302 of an intraoperative microscope. A large-diameter objective 304 is installed inside the tip of a lens barrel 291. An image formed on the objective 304 is enlarged with variable power lenses (for varying magnifying powers) 305a and 305b arranged off an optical axis of the objective 304 but in parallel with the optical axis, then emitted to half-prisms 306a and 306b.

Light beams passing through the half-prisms 306a and 306b are formed on image formation lenses 307a and 307b, then enlarged with eyepieces 308a and 308b. Finally, an observation object image of an operated region 310 or other an observation object region is formed on retinae and thus visualized three-dimensionally.

Relay lenses 311a and 311b are arranged to oppose the half-prisms 306a and 306b, which provide the half-prisms 306a and 306b with computer graphic (hereafter, CG) images on monitors 312a and 312b for displaying CG images sent from a control and power supply 303. Part of CG images on the monitors 312a and 312b is reflected by the half-prisms 306a and 306b. After passing through the image formation lenses 307a and 307b and the eyepieces 308a and 308b, similarly to light passing through the half prisms 306a and 306b, the reflected CG images are seen three-dimensionally by a surgeon.

Figure 37:
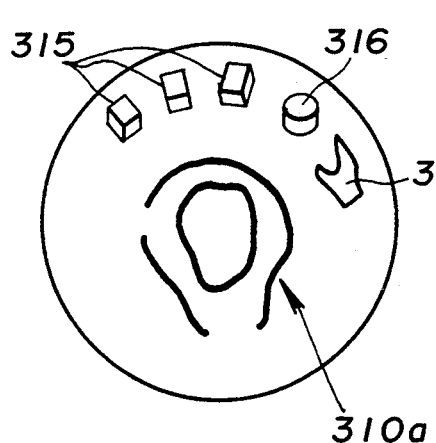

Therefore, in the surgeon's observation field of view, the CG images of the monitor 312a and 312b are superimposed on the observation object image as shown in FIG. 37.

As shown in FIG. 38, a lens barrel 291 of a main unit 302 of an intraoperative microscope is mounted on a stand 294 or other supporting body via a movable arm 293 equipped with a fine movement adjustment mechanism 292. For example, when the fine movement adjustment mechanism 292 is driven, the lens barrel 291 can be moved on, for example, a horizontal plane two-dimensionally. When a mounting mechanism 295 of the stand 294 is driven, the lens barrel 291 can be moved vertically. When part of the lens barrel 201 is moved in the optical-axis direction, focusing or zooming can be done. These facilities can be actuated by selecting the specific switches from among multiple switches. A facility relative to a selected switch can be set to an intended zooming value using a handle which is formed on the fine movement adjustment mechanism 292 or mounting mechanism 295. The handle is not illustrated. In this embodiment, pseudo switches and handles are displayed in an observation field of view in association with the foregoing facilities. A pseudo operation member in the observation field of view is used to activate an intended facility.

For detecting the position of a surgeon's hand 313, an ultrasonic position sensor B 314b is put on the hand 313. An ultrasonic position sensor A 314a is also installed to detect the position of the ultrasonic position sensor B 314b. The output of the position sensor A 314a is supplied to a control and power supply 303. Then, the control and power supply 303 displays CG images on monitors 312a and 312b so that the CG images will appear at an appropriate position in an observation field of view which corresponds to the position of the ultrasonic position sensor B 314b.

For example, as shown in FIG. 37, multiple pseudo switches 315, a pseudo handle 316, and a pseudo switch/handle operation member 317 for selecting any of the pseudo switches 315 and handle 316 are visualized in the observation field of view around an observation object image 310.

The pseudo switch/handle operation member 317 is a CG image having, for example, a hand-like shape. When a hand 313 is moved, the pseudo switch/handle operation member 317 moves to a position corresponding to the position of the hand 313. Thus, any of the pseudo switches 315 or the pseudo operation handle 317 can be selected.

When the pseudo switch/handle operation member 317 is moved to any of the pseudo switches 315 or the pseudo operation handle 316, a control and power supply 303 generates a control signal relative to the selected pseudo switch 315 or the pseudo operation handle 316. The control signal selects and drives, for example, a fine movement adjustment mechanism of a main unit 302 of an intraoperative microscope.

Figure 35:
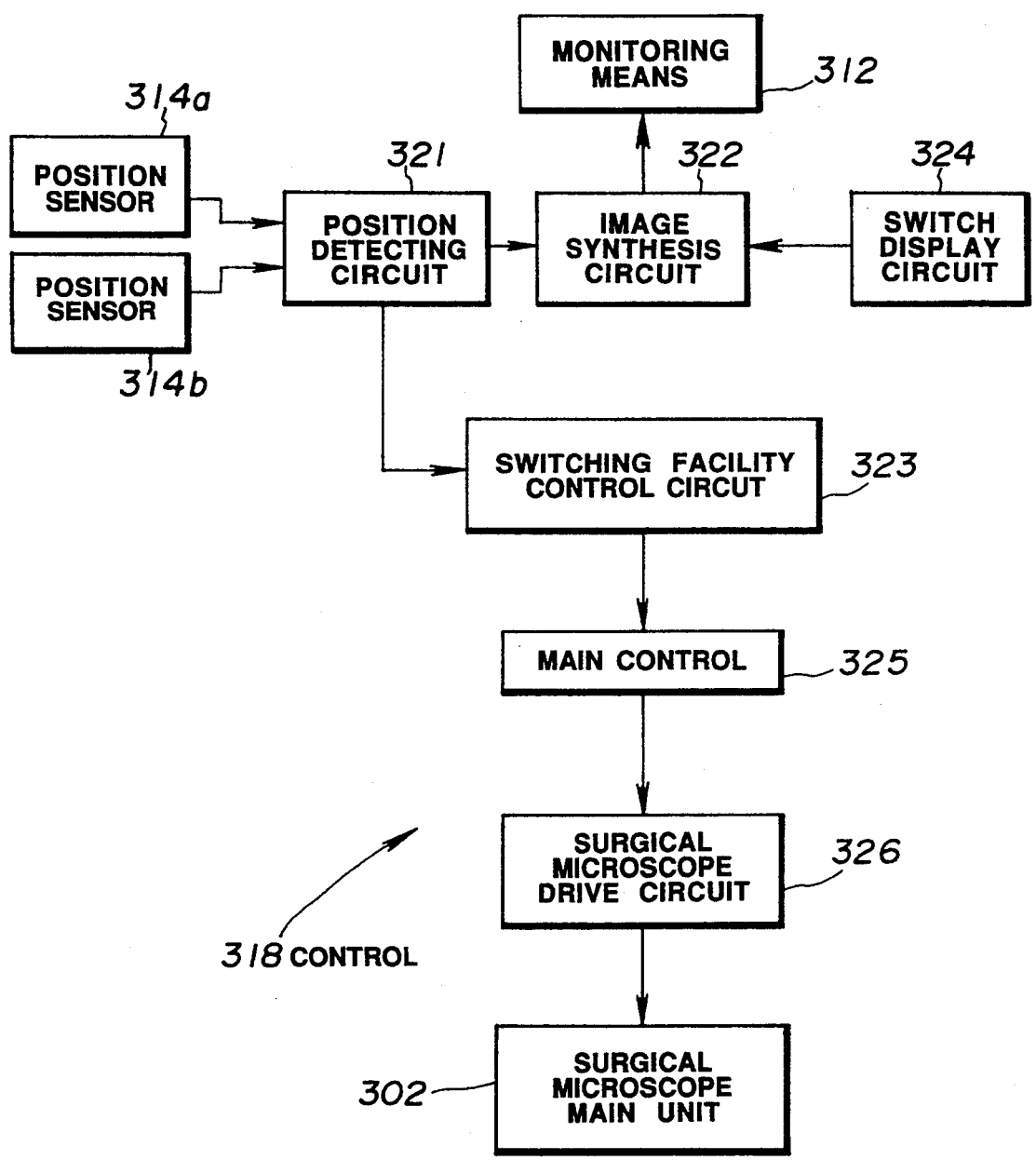
FIGS. 35 to 38 relate to the ninth embodiment.

FIG. 35 shows the configuration of a control section 318 of a control and power supply 303. Outputs of a position sensor A 314a and a position sensor B 314b are supplied to a position detecting circuit 321. The position detecting circuit 321 detects the position of a hand 313 to calculate the position of a pseudo switch/handle operation member 317 associated with the hand 313. The output of the position detecting circuit 321 is supplied to an image synthesis circuit 322 and to a switching control circuit 323.

The image synthesis circuit 322 synthesizes a CG image showing pseudo switches 315 and a pseudo operation handle 316 a switch display circuit 324 generates and a CG image of a pseudo switch/handle operation member 317, then displays the synthetic image on monitors 312a and 312b (represented as a monitoring means 312 in FIG. 35).

The switching control circuit 323 generates a select signal for activating the selected pseudo switch 315 or pseudo operation handle 316. The select signal of the control circuit 323 is supplied to a main control section 325. According to the input select signal, the main control section 325 provides an intraoperative microscope drive circuit 326 with a control signal for activating the function of the selected pseudo switch 315 or pseudo operation handle 316, and thus controls the state of a main unit 302 of an intraoperative microscope or zooming of the main unit 302 according to the selected pseudo switch 315 or pseudo operation handle 316.

The pseudo operation handle 316 drives a facility for moving a main unit of an intraoperative microscope up, down, left, or right, or zooming up or down the main unit depending on whether the pseudo switch/handle operation member 317 is set in the upper or lower part.

According to the ninth embodiment, a surgeon can control drive of an intended facility by selecting the corresponding pseudo switch 315 or pseudo operation handle 316 from an observation field of view using a pseudo switch/handle operation member 317 associated with the movement of a hand 313. That is to say, a surgeon can operate any of the pseudo switches 315 or the pseudo operation handle 316 visualized near an operated region 310. This realizes an user-friendly operation means which does not intervene a surgical procedure.

A surgeon can operate switches while observing an observation field of view. From this viewpoint, a user-friendly intraoperative microscope is realized. In the past, a surgeon has had to distract his/her visual line from an eyepiece unit when operating switches. In this embodiment, a surgeon need not to distract his/her visual line. This results in a shortened operation time or a reduced fatigue. Thus, a use-friendly intraoperative microscope is realized. Pseudo switches can be arranged in a field of view using corresponding graphics whatever the spatial sizes of the actual switches are. When an intended pseudo switch is specified in the field of view, an intraoperative microscope operates in the same manner as when the corresponding switch is pressed actually.

In conventional intraoperative microscopes, their operation units must be manipulated actually. Therefore, the vicinity of the operation unit is likely to become dirty. In this embodiment, a graphic corresponding to an actual switch is selected merely by moving a hand 313. This helps keep clean the vicinity of the operation unit. The arrangement of switches can be changed on monitors as a surgeon likes. Switches displayed are available in various sizes.

Even if an intraoperative microscope is moved drastically during grafting, switches need not be dragged unlike conventional intraoperative microscopes. Conventionally, a surgeon has proceeded with a surgical procedure on his/her feet or in his/her seat, or requires a dedicated switch depending on his/her skill. This embodiment obviates such a dedicated switch. Conventional switches and pseudo switches in a field of view may be used selectively.

Next, the tenth embodiment of the present invention will be described.

Figure 39:
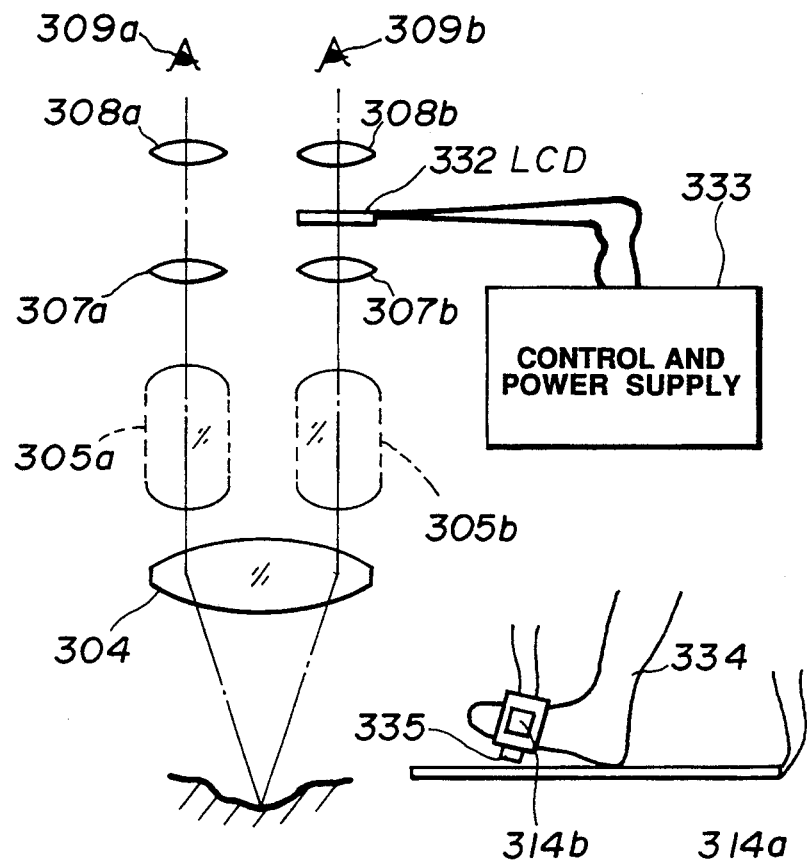
FIGS. 39 to 41 relate to the tenth embodiment of the present invention.

In an intraoperative microscope of the tenth embodiment shown in FIG. 39, a penetrating LCD 332 is interposed between an image formation lens 307b and an eyepiece 308b instead of half-prisms 306a and 306b and monitors 312a and 312b in FIG. 36. The LCD 332 is controlled by a control and power supply 333. In this embodiment, a position sensor 314b is put on a foot 334. A plate-type position sensor 314a is laid down to detect the position of the foot 334.

Figure 40:
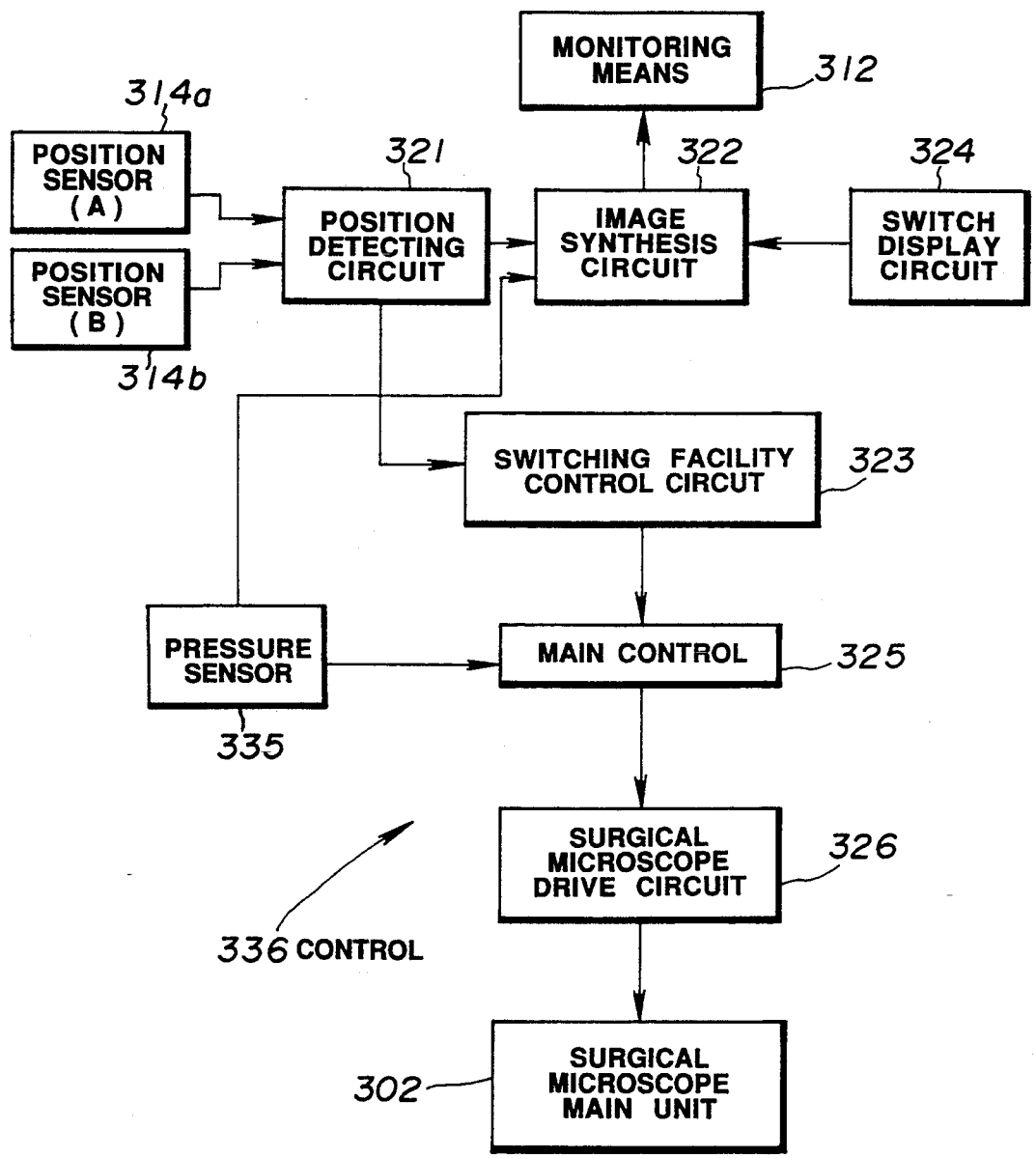

The foot 334 is provided with a pressure sensor 335 serving as a mechanical switch. In a control section 336 of this embodiment shown in FIG. 40, additionally to that shown in FIG. 35, a pressure sensor 335 also supplies an output to an image synthesis circuit 322 and to a main control section 325.

Figure 41:
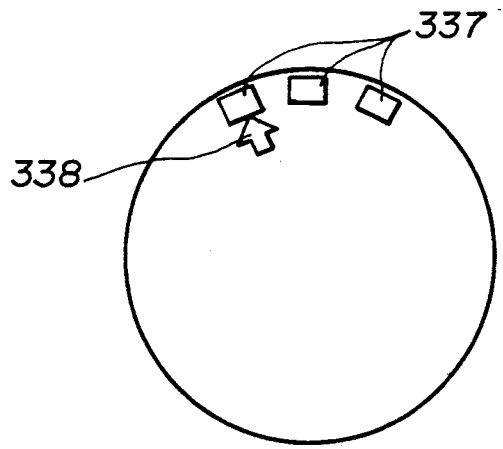

In this embodiment, flickering of the elements of an LCD 332 is controlled so that rectangular pseudo operation switches 337 and an arrow-shaped pseudo switch operation member 338 will appear in an observation field of view as shown in FIG. 41. The identification of multiple rectangular pseudo operation switches 337 are indicated with symbols within the rectangles.

Other components are identical to those of the ninth embodiment. The description will be omitted. In this embodiment, an LCD 332 is used to display pseudo operation switches 337 in an observation field of view. A position sensor 334b is put on a surgeon's foot 334 and a position sensor 334a is laid down to detect the position of the position sensor 334b. At the position in the field of view corresponding to the position of the position sensor 334b, a CG image on the LCD 332 is arranged to show a pseudo switch operation member 338.

When a foot 334 is moved, a pseudo switch operation member 338 is moved accordingly. When the pseudo switch operation member 338 is positioned at an intended pseudo operation switch 337, the foot 334 is stepped down to turn on a switch of a pressure sensor 335. Then, a control section 325 is informed of the fact that the pseudo operation switch 337 the pseudo switch operation member 338 points to has been specified. Then, a facility associated with the pseudo operation switch 337 is driven. In this embodiment, the facilities of the ninth embodiment can be realized with lower costs.

In this embodiment, a handle is not included but may be installed.

Figure 42:
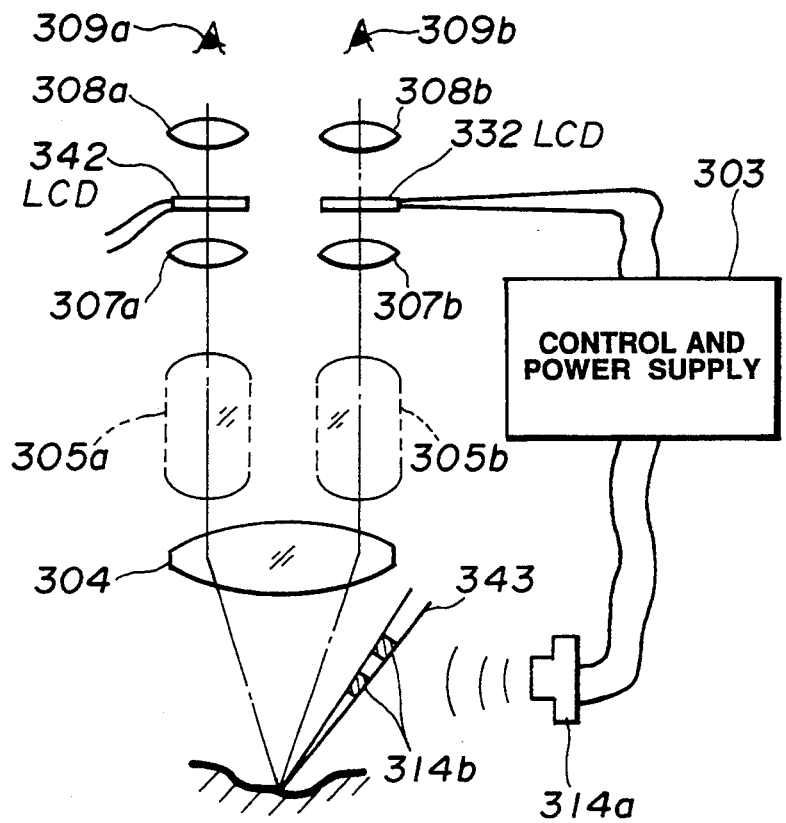
FIGS. 42 and 43 relate to the eleventh embodiment of the present invention.

FIG. 42 shows the configuration of an optical system for a main unit of an intraoperative microscope in the eleventh embodiment.

In this embodiment, operation switches for an intraoperative microscope are displayed in an observation field of view to assist a surgeon in using tweezers or another surgical tool.

As shown in FIG. 42, in this embodiment, additionally to that of FIG. 39, an LCD 342 is interposed between an image formation lens 307a and an eyepiece 308a. In this embodiment, a position sensor 314b is incorporated in a surgical tool 343. A position sensor 314a detects the position of the position sensor 314b. A control section in this embodiment has the same configuration as that of FIG. 35 in principal. Therefore, the configuration diagram is not appended.

Figure 43:
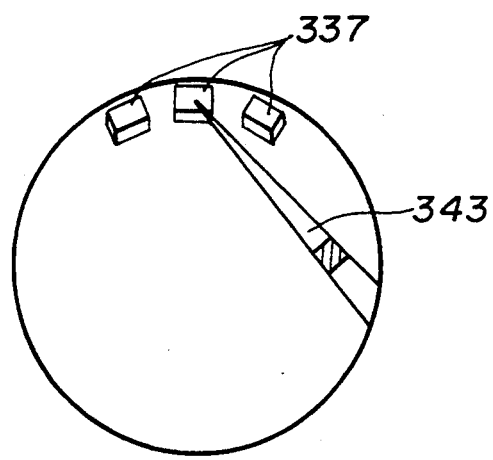

Two LCDs 332 and 342 are installed, allowing pseudo operation switches 337 to appear three-dimensionally in an observation field of view as shown in FIG. 43. In this embodiment, a pseudo switch operation member is not displayed. An actual surgical tool 343 is used to specify the pseudo operation switches. This ensures ease of operation.

The operation and effects of this embodiment are almost identical to those of the ninth embodiment.

Figure 44:
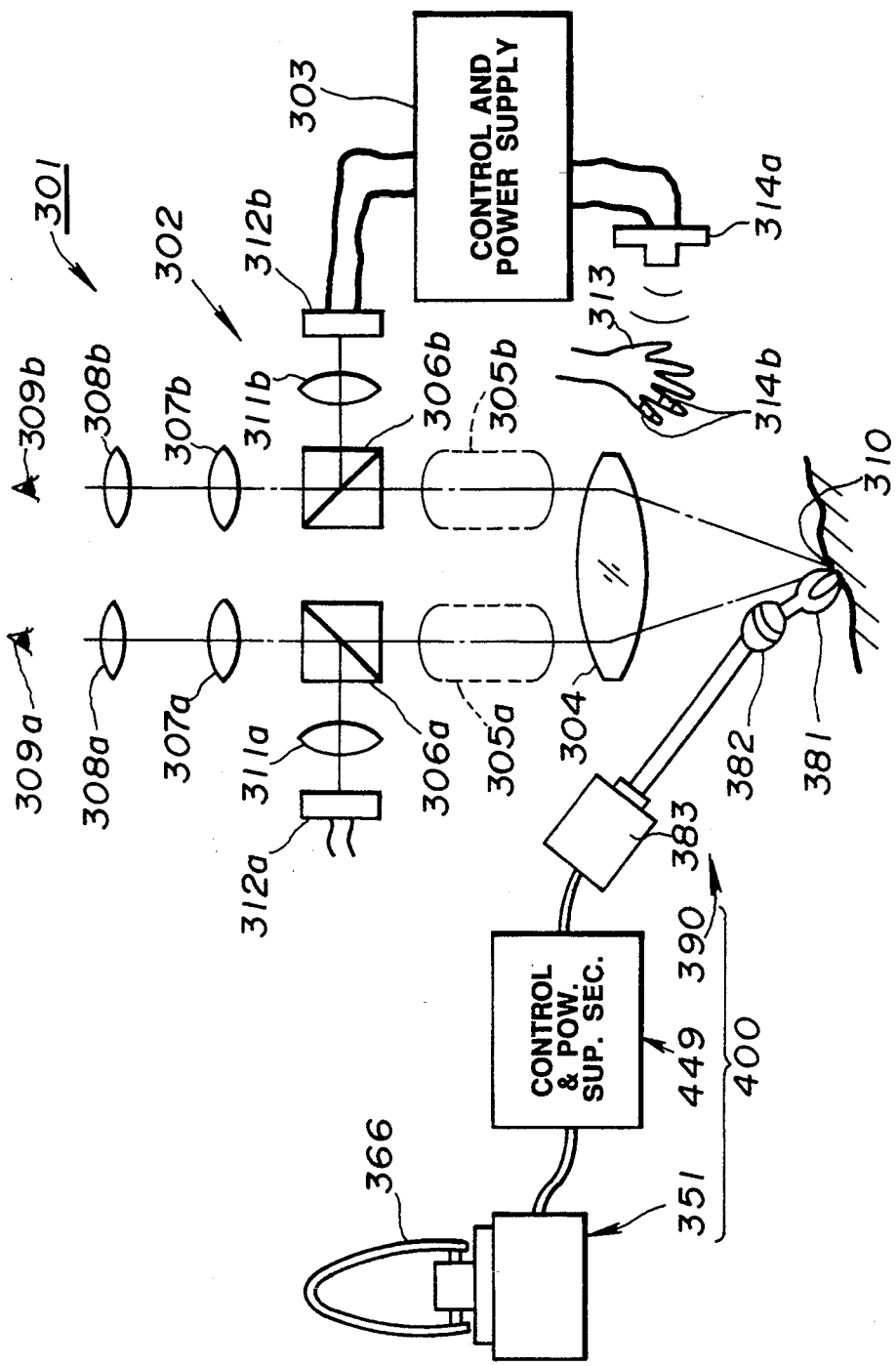
FIGS. 44 to 49 relate to the twelfth embodiment of the present invention.

FIG. 44 shows an intraoperative microscope apparatus of the twelfth embodiment. This apparatus has a needle holder 400 in addition to an intraoperative microscope 301 shown in FIG. 9.

A surgical needle or other surgical tool of an intraoperative microscope must be positioned precisely. This embodiment has a needle holder 400 made up of an operation unit for precise positioning and an operating section (treatment section) which operates according to the manipulation of the operation unit.

The needle holder 400 comprises an operation unit 351 a surgeon manipulates, a control and power supply for performing signal processing to pass control according to the manipulation of the operation unit 351, and an operating section 390 which operates according to the manipulation of the operation unit 351. The operation unit 351 has a grasping (holding) section a surgeon grasps (holds) for manipulation.

Figure 45:
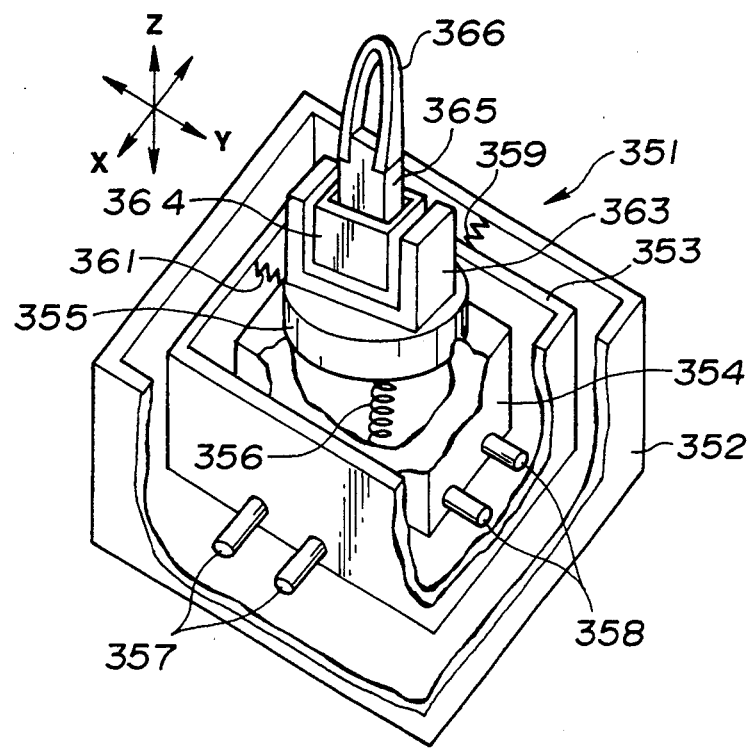

As shown in FIG. 45, in the operation unit 351 a surgeon manipulates, a first moving base 354 is stored in an inner case 343 encased in an outer case 352, and a second moving base 355 is mounted on the first moving base 354 via an air spring 356. The inner case 353 is mounted on the outer case 352 using guide axes 357 extending in the X-axis direction so that the inner case 353 can move freely. The first moving base 354 is mounted on the inner case 353 using guide axes extending along the Y axis orthogonal to the X axis so that the first moving base 354 can move freely.

The inner case 353 is coupled elastically to the outer case 352 using an air spring 359 extending in the X-axis direction. The first moving base 354 is coupled elastically to the inner case 353 using the air spring 361 extending along the Y axis.

Figure 46:
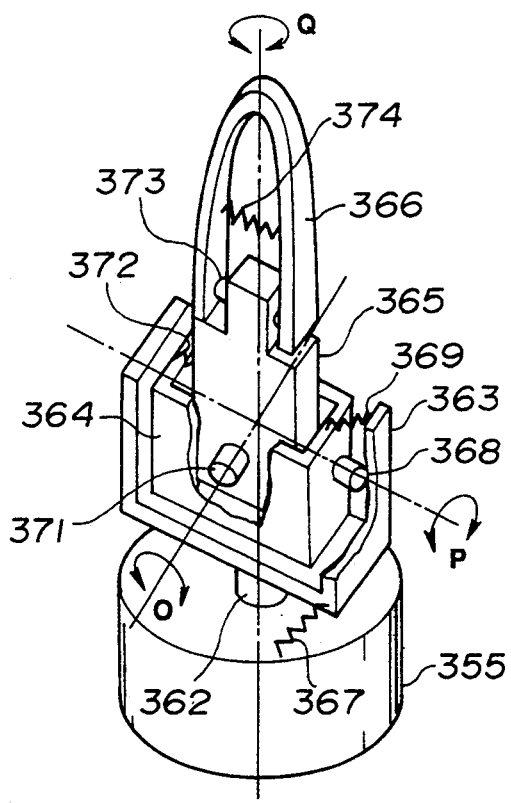

On the second moving base 355, a rotation axis 362 is, as shown in FIG. 46, projecting upward (along the Z axis) orthogonal to the XY plane, and an outer frame 363 is mounted around the center axis (indicated with Q) to rotate freely. The outer frame 363 accommodates an inner frame 364. A holding section 366 a surgeon manipulates is mounted in the inner frame via a holding base 365.

The outer frame 363 is coupled elastically to the second moving base 355 using an air spring 367. A rotation axis 368 is projecting from the inner frame 364. The outer frame 363 is mounted to freely rotate about the rotation axis 368 (indicated with P). The inner frame 364 is coupled elastically to the outer frame 363 using an air spring 369.

A rotation axis 371 is projecting from the holding base 365. The holding base 365 is mounted on the inner frame 364 to rotate freely about the rotation axis 371 (indicated with O). The holding base 365 is coupled elastically to the inner frame 364 using an air spring 372.

An axis 373 is projecting from the top end of the holding base 365. The proximal ends of the holding section 366 are engaged with the axis 373. An air spring 374 is installed on opposing inner surfaces of the holding section 366. The holding section 366 can move in the pinching direction and tilt about the O, P, or Q axis.

Figure 47:
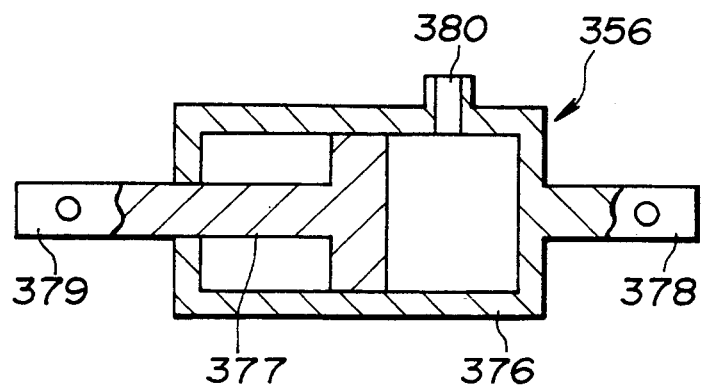

Each air spring (for example, 356) is, as shown in FIG. 47, made up of a housing 376, a piston 377 to be fitted into the housing 376, and support ends 378 and 379 formed as part of the housing 376 and piston 377. When air is pumped in or out from a space created with the piston 377 through an air inlet/outlet 380, the air spring functions as a tension or compression spring. The spring force is adjustable.

Figure 48:
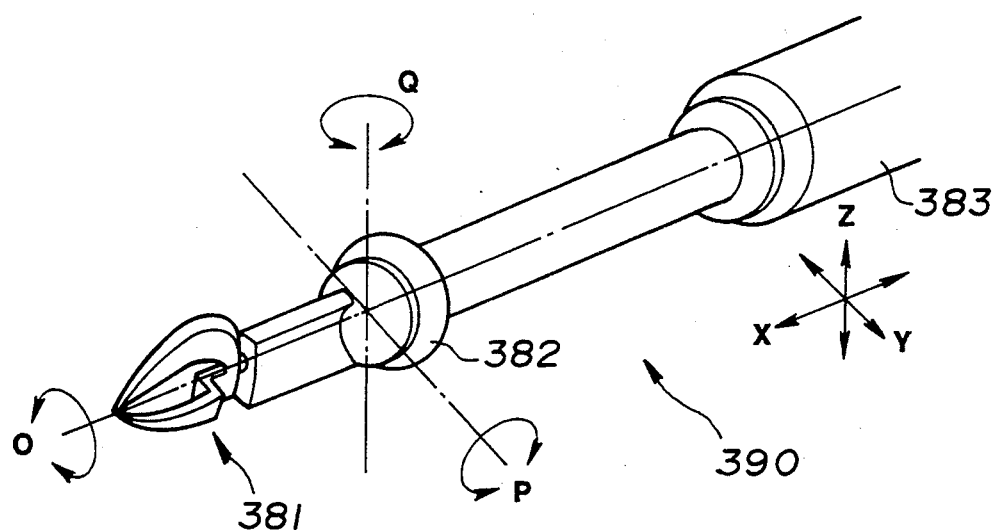

FIG. 48 shows an operating section 390 which operates in association with the manipulation of an operation unit 351. A needle holder 381 can tilt about the O, P, or Q axis using an angle changer 382 which is coupled to a moving section 383. A motor serving as a power source, which is not shown, and a wire serving as a transmission member, which is not shown, drive the needle holder 381 in association with the X, Y, or Z, or O, P, or Q, or pinching movement of an operation unit 351.

A scale is printed on one side of a relatively-moving portion of an operation unit 351, and a photo-detector is arranged on other side, so that a moving rate can be calculated. Then, an operating section 390 is moved at a rate corresponding to the moving rate. When the operating section 390 touches an operated region and generates a resistance, the current value of a motor increases. Then, a corresponding resistance is generated for the operation unit 351 by controlling an air spring. With this resistance, a surgeon can perceive information related to the operated region; such as, stiffness, stretching, or twisting.

Figure 49:
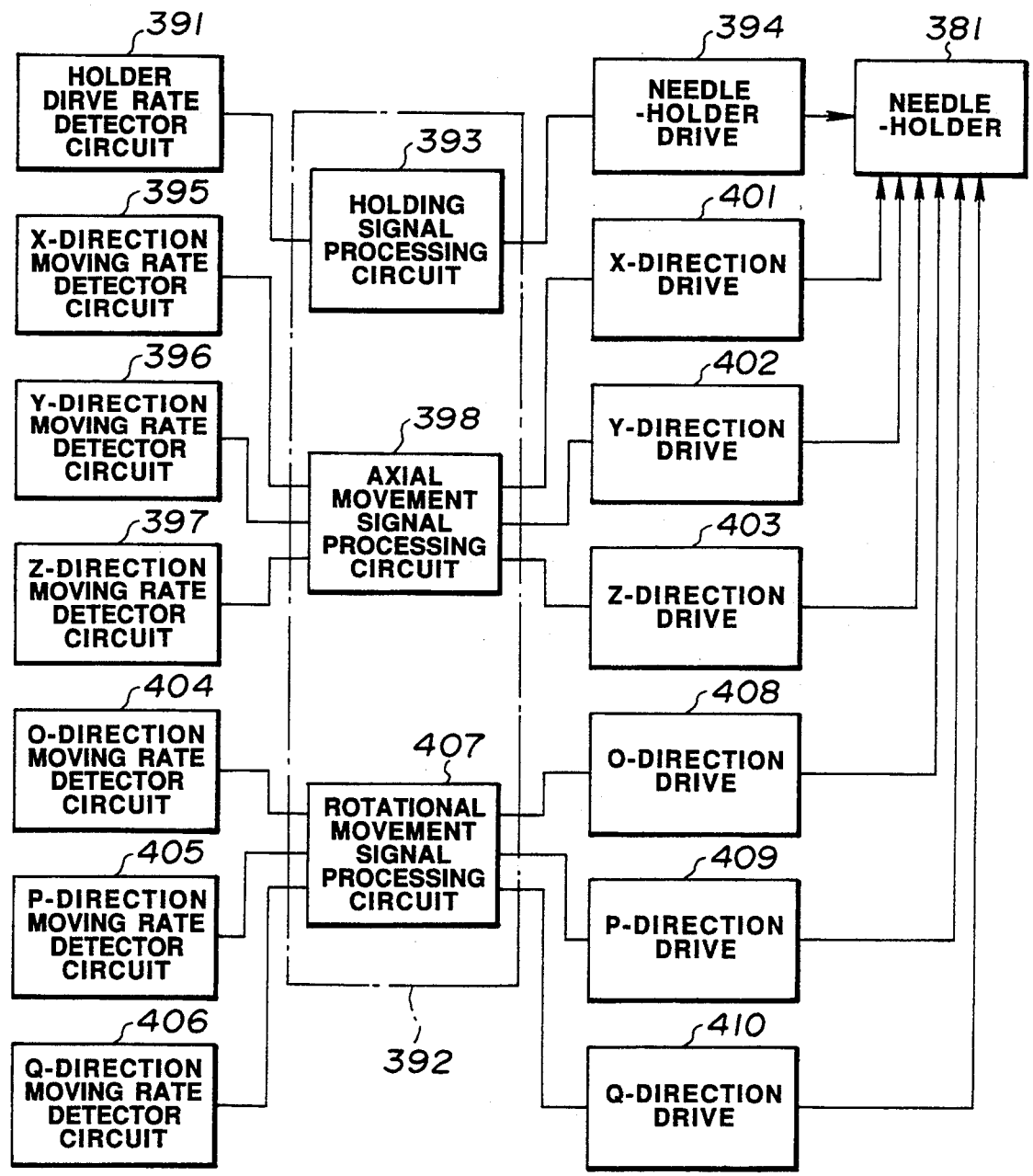

FIG. 49 shows the configuration of a control section for electrically and mechanically controlling an operating section of a needle holder 381. An output of a holding section driving rate detector 391 is fed to a holding signal processing circuit 393 of a signal processor 392. Then, a holding signal is generated to drive the needle holder 381 via a needle holder drive 394. Outputs of an X-direction moving rate detector 395, an Y-direction moving rate detector 396, and a Z-direction moving rate detector 397 are supplied to an axial movement signal processing circuit 398. Then, axial movement signals are generated, which, then, drive the needle holder 381 via an X-direction drive 401, an Y-direction drive 402, and Z-direction drive 410.

Outputs of an O-direction moving rate detector 404, a P-direction moving rate detector 405, and Q-direction moving rate detector 406 are supplied to a rotational movement signal processing circuit 407. Then, rotational movement signals are generated, which, then, drive the needle holder 381 via an O-direction drive 408, a P-direction drive 409, and a Q-direction drive 410.

Figure 50:
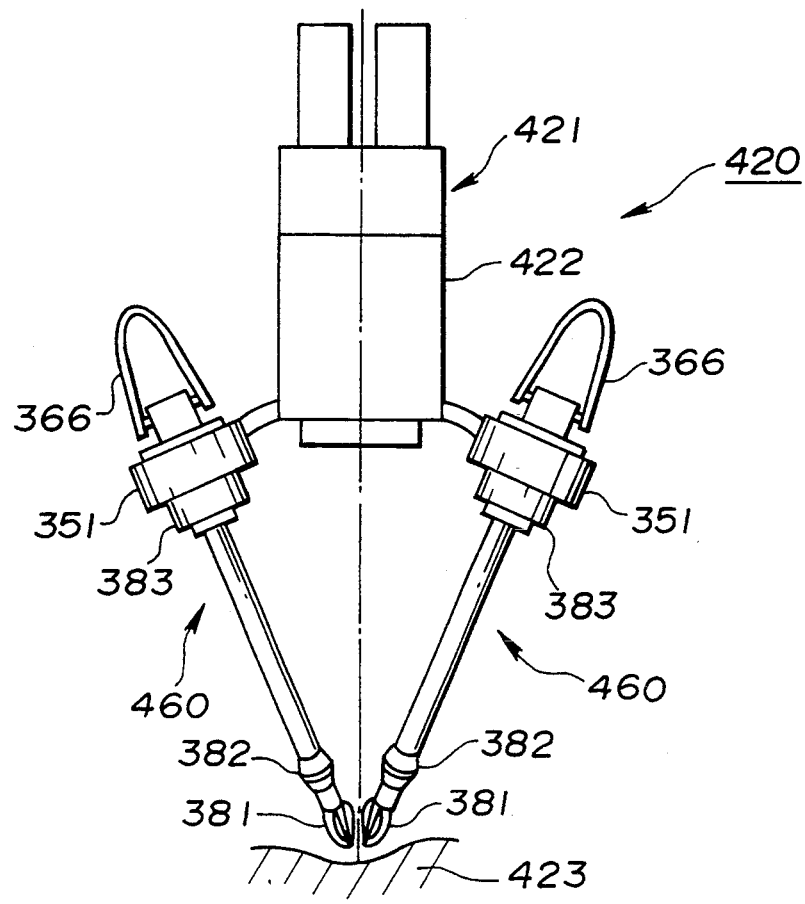
FIGS. 50 to 52 relate to the thirteenth embodiment of the present invention.

FIG. 50 shows an intraoperative microscope apparatus 420 of the thirteenth embodiment. The apparatus 420 includes two needle holders 460. An operation unit 351 is mounted on each side of a lens barrel 422 of a main unit 421 of an intraoperative microscope using a supporting member. An operating section is formed on the front of each operation unit 351. Then, using a holding section 366 on the top of each operation unit 351, a needle holder 381 can be operated via a moving section 383 and an angle changer 382 to treat an operated region 423.

Figure 51:
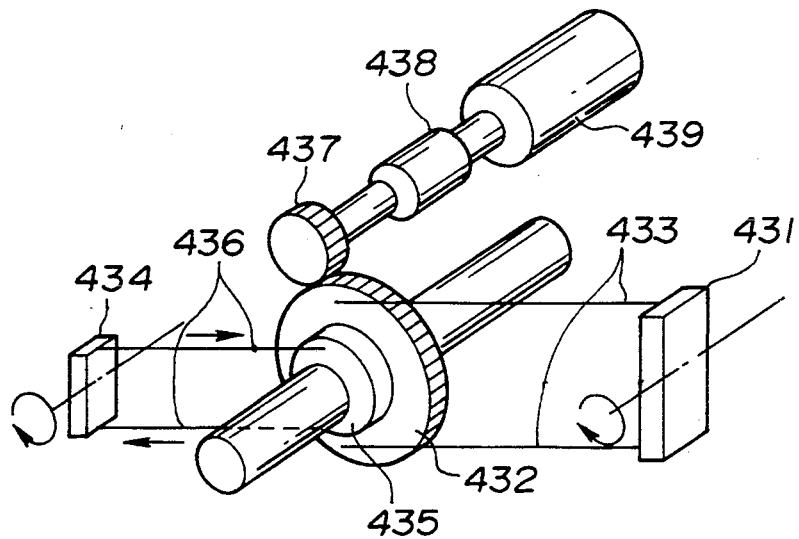

The operating section is a needle holder 381 or a shear, permitting microvascular anastomosis. The relationship between an operation unit 351 and an operating section in this embodiment will be described in conjunction with FIG. 51. In this example of an angle changer 382, an operation member 431 and a first disk 432 are linked with a wire 433, and an operating member 434 and a second disk 435, with a wire 436. Both the disks 432 and 435 rotate around an axis, and connected with a torsion coil spring which is not shown.

A gear is formed on the circumference of the first disk 432. The gear is engaged with a smaller-diameter gear 437. The gear 437 is coupled to an actuator 439 via a torsion bar 438.

The moving rate of the operation member 431 is also used as a rate for moving the operating member 434 directly and mechanically. When resistance occurs at an operated region, the torsion coil spring is wound up or down to cause a rotation shift. The actuator 439 moves the first disk 432 forcibly in a direction for correcting the rotation shift. This allows the operation member 431 to generate a large operation resistance.

The actuator 439 is made up of a stepping motor and a reducing gear including a worm and a worm wheel for preventing inverse rotation. Operation resistance is given by a torsion bar 438. This embodiment provides higher performance than the twelfth embodiment.

Figure 52:
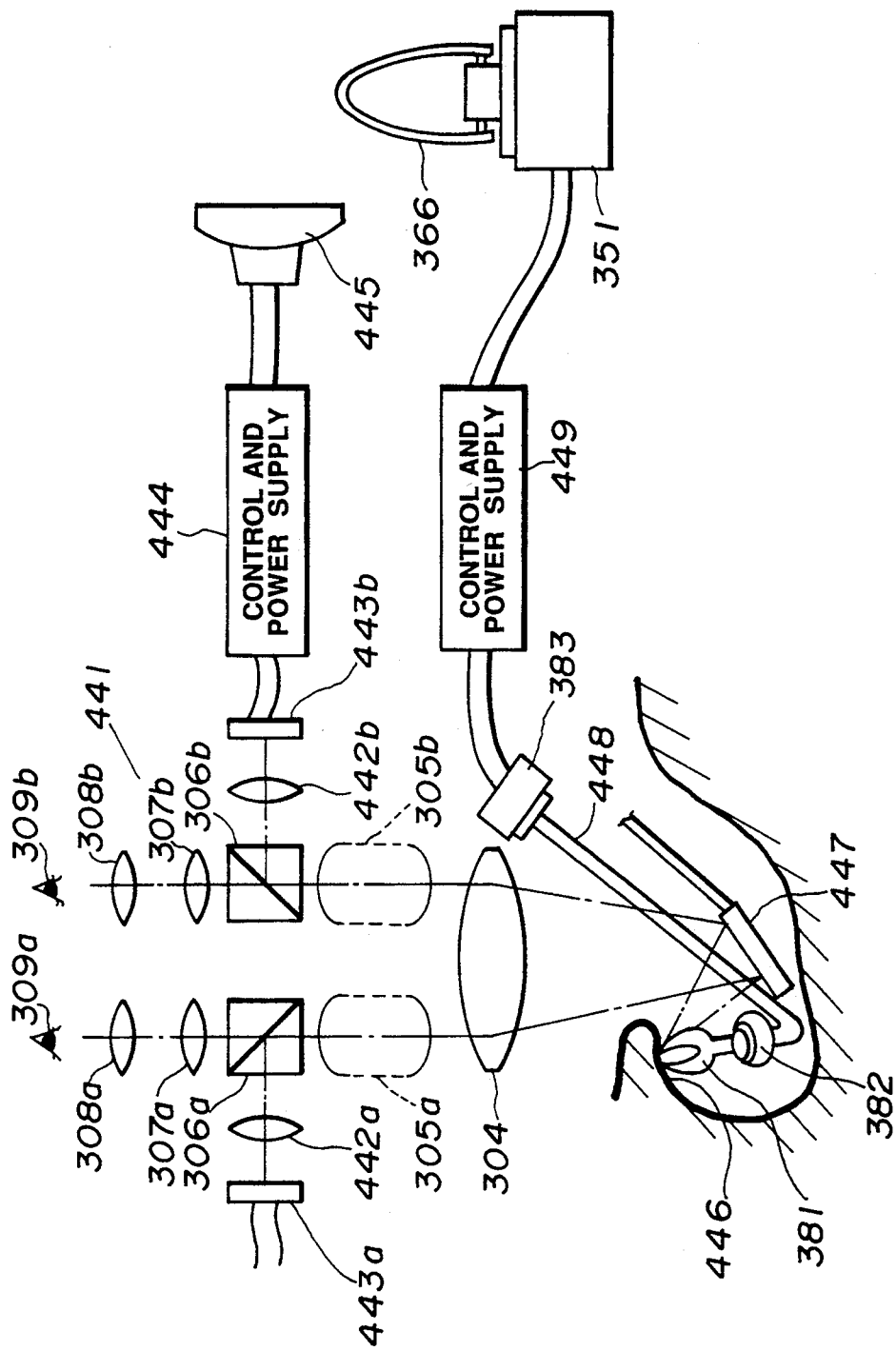

FIG. 52 shows a variant of the thirteenth embodiment. A main unit 441 of an intraoperative microscope has image formation lenses 442a and 442b and imaging devices 443a and 443b in TV cameras. Images acquired by the imaging devices 443a and 443b are displayed on a monitor 445 via a control and power supply 444. Thus, an operated region can be observed three-dimensionally.

The main unit 441 of an intraoperative microscope is, in principle, identical to that shown in FIG. 36. The components will be indicated with the same symbols. In this variant, half-prisms 306a and 306b bifurcate light beams coming from variable power lenses 305a and 305b, then form images of an operated region 446 on imaging devices 443a and 443b via image formation lenses 442a and 442b. In FIG. 52, the image of the operated region 446 is reflected by a mirror 447 and guided to an objective 304.

In this variant, a needle holder 381 is coupled to a moving section 383 via an angle changer 382 and a bent bar member 448. The moving section 383 is connected to a control and power supply 449 via a cable. The control and power supply 449 is connected to an operation unit 351 via a cable. When a holding section 366 is manipulated, the needle holder 381 can be operated remotely. FIG. 52 shows a scene of operating an operated region 446 on the reverse side of a body cavity on which surgery cannot be performed normally.

In this variant, similarly to the previous embodiment, a needle holder can be operated remotely. The vicinity of a surgeon is straightened up. This allows the surgeon to proceed smoothly with treatment. A surgical procedure can proceed between, for example, Tokyo and New York over a telephone line.

If a needle holder and a shear can be changed automatically as performed in, for example, a machining center, surgical tools need not be changed with hands.

Next, an intracorporeal treatment apparatus will be described.

Figure 53:
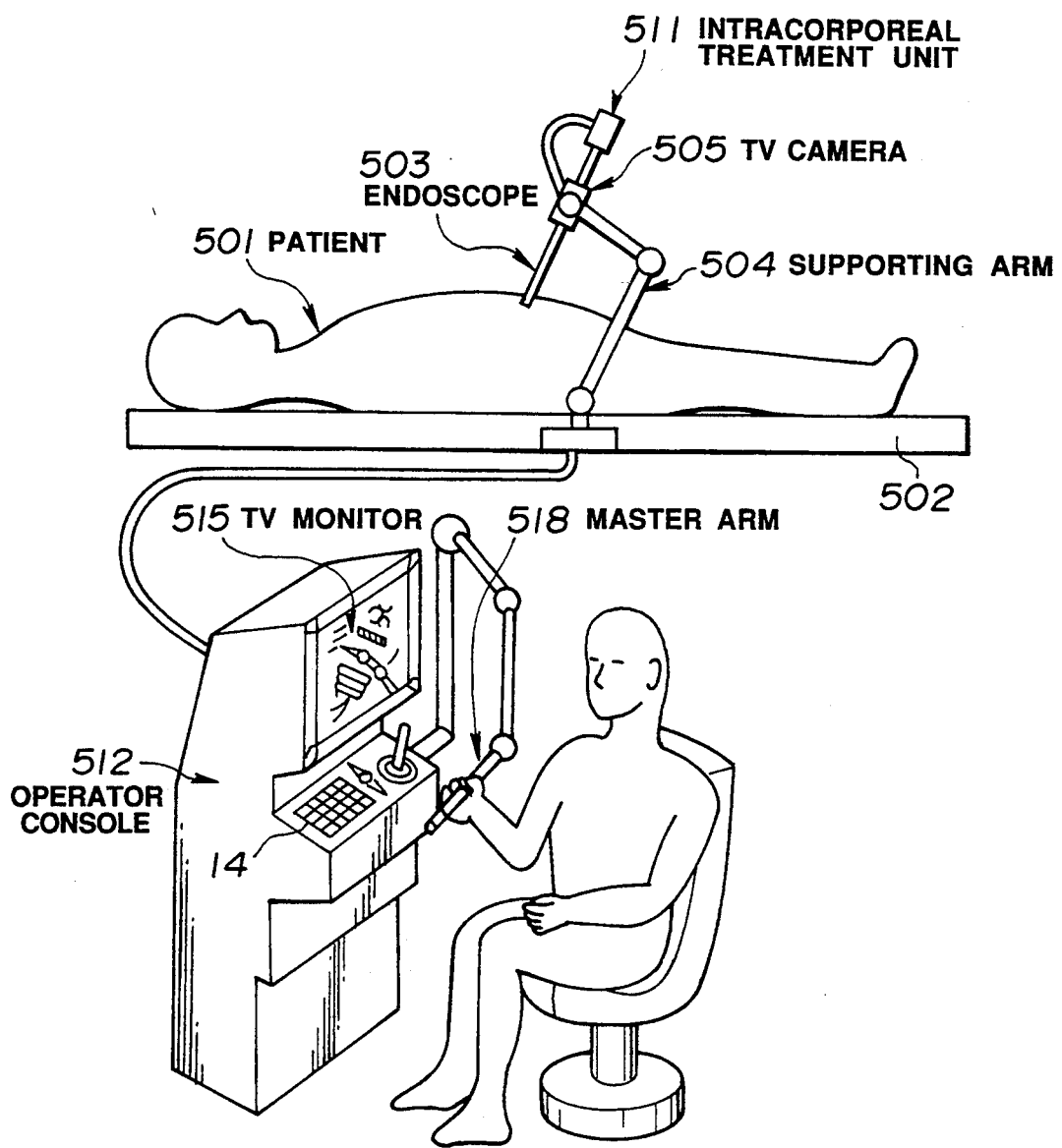
FIG. 53 is an explanatory diagram showing the schematic configuration of an entire intracorporeal treatment apparatus of the fourteenth embodiment of the present invention.
Figure 54:
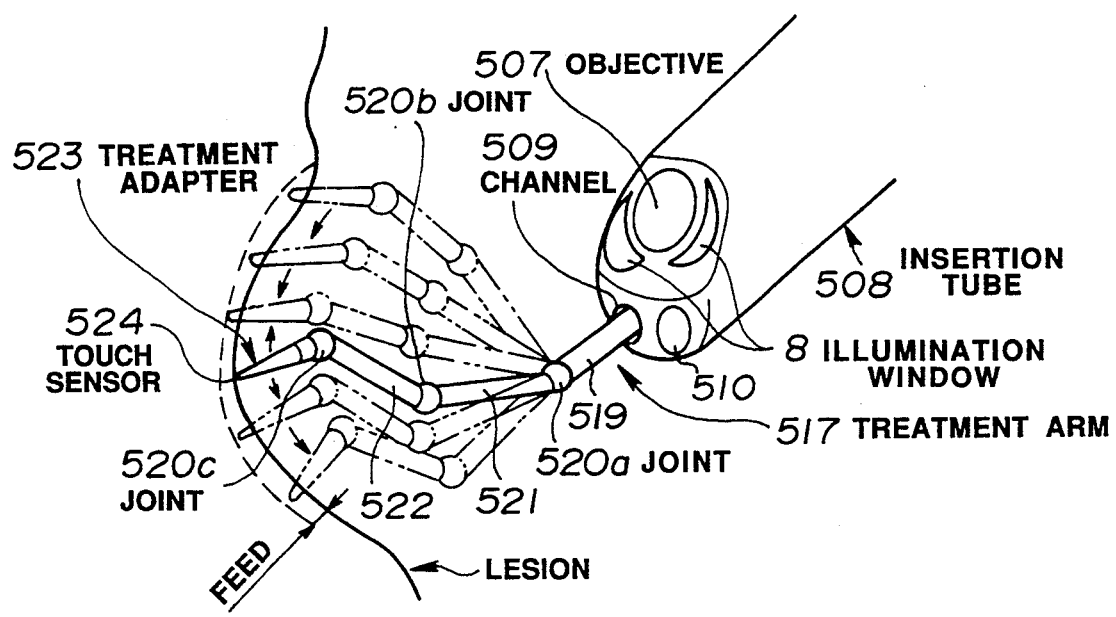
FIG. 54 is an oblique view of an intracorporeal insertion tube of the intracorporeal treatment apparatus of the fourteenth embodiment.

FIG. 53 shows the schematic configuration of an entire intracorporeal treatment apparatus. A support arm 504 for supporting an endoscope 503 is mounted on an operating table 502 on which a patient lies. The endoscope 503 has a conventional configuration, and is, for example, a rigid endoscope. The external end of the endoscope 503 is provided with a TV camera 505. An insertion tube 506 of the endoscope 503 is inserted into a body using a trocar for puncturing a patient's abdomen. FIG. 54 shows the inserted insertion tube 506 of the endoscope 503. At the tip of the insertion tube 506 of the endoscope 503, the tips of two channels 509 and 510 as well as an objective 507 and an illumination window 508 are opening. An intracorporeal treatment apparatus 511 to be described later is running through one channel 509.

An operator console 512 for operating the intracorporeal treatment apparatus 511 is installed near the operating table 502. The operator console 512 has a keyboard 514 and a TV monitor 515. The TV monitor 515 visualizes the states of a body acquired with the tip of the insertion tube 506 of the endoscope 503 inserted.

An electronic control circuit 516 to be described later is incorporated in the operator console 512. A master arm 518 which moves in association with a treatment arm 517 of the intracorporeal treatment apparatus 511 at a 1-to-1 ratio of moving force or with a proportional moving force is installed on the operator console 512.

The tip of an introducing section 519 of an intracorporeal treatment apparatus 511 is coupled to a treatment arm 517. The treatment arm 517 includes the tip of the introducing section 519, a first link 521, a second link 522, and a treatment adapter 523 which are coupled sequentially via joints 520a, 520b, and 520c. A touch sensor 524 for sensing the contact of the treatment adapter 523 with a living tissue and its strength is installed in the tip of the treatment adapter 523.

Figure 55:
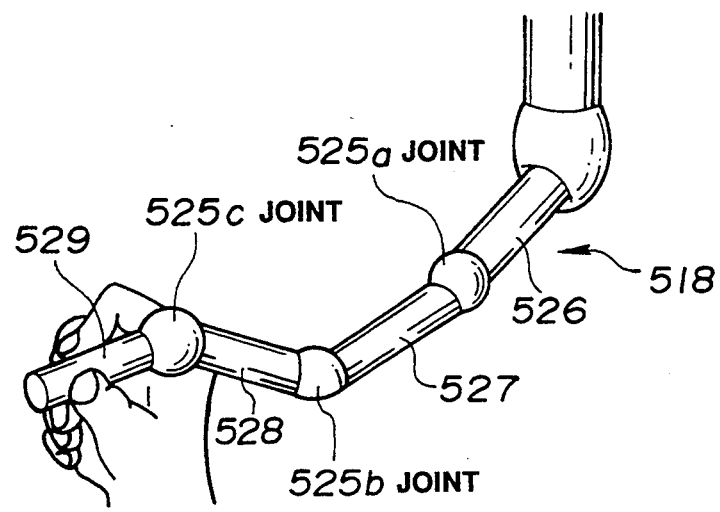
FIG. 55 is an oblique view of a master arm of the intracorporeal treatment apparatus.

A master arm 518 which is associated with a treatment arm 517 of an intracorporeal treatment apparatus 511 at a 1-to-1 ratio of moving force includes, as shown in FIG. 55, a proximal link 526, a first link 527, a second link 528, and a grasping section 529 which are coupled sequentially via joints 525a, 525b, and 525c. A surgeon holds the grasping section 529 to manipulate it.

Bending drive actuators A, B, and C, and brake actuator $\alpha$, $\beta$, and $\gamma$ are incorporated in the joints 520a, 520b, and 520c of the treatment arm 517 of the intracorporeal treatment apparatus 511. The joints 520a, 520b, 520c, 525a, 525b, and 525c are provided with potentiometers a, b, and c for detecting displacement driving rates.

Figure 56:
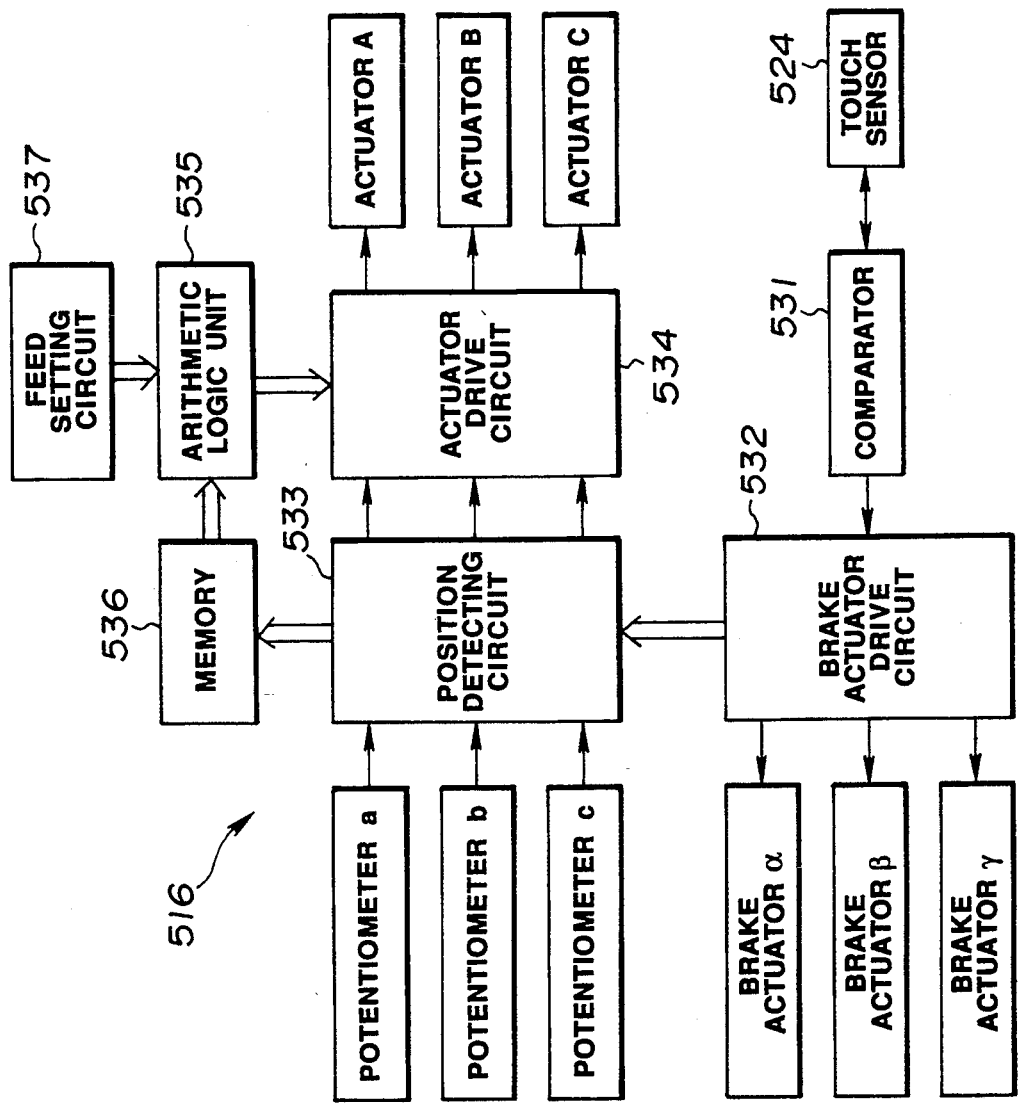
FIG. 56 is an explanatory diagram of an electronic control circuit in the intracorporeal treatment apparatus.

As shown in FIG. 56, in an electronic control circuit 516, a comparator 531 handles an output of a touch sensor 524 to generate a signal indicating a state of contact and its strength, then provides a brake actuator drive circuit 532 with the signal. The brake actuator drive circuit 532 drives brake actuators $\alpha$, $\beta$, and $\gamma$ according to the state of contact. The information is supplied to a position detecting circuit 533. The position detecting circuit 533 receives detection signals from potentiometers a, b, and c and detects the bending positions of joints 520a, 520b, 520c, 525a, 525b, and 525c. An actuator drive circuit 534 receives signals from the position detecting circuit 533 and an instruction from an arithmetic logic unit 535, then operates bending drive actuators A, B, and C. The bending position information of the joints 520a, 520b, 520c, 525a, 525b, and 525c is temporarily stored in a storage circuit 536. Using the information, the arithmetic logic unit 535 drives the actuator drive circuit 534. A feed setting circuit 537 for setting a feed of a treatment adapter 523 is installed for profiling.

FIGS. 57 and 58 show examples of bending drive actuators A, B, and C, and brake actuators $\alpha$, $\beta$, and $\gamma$ installed in joints 520a, 520b, 520c, 525a, 525b, and 525c. Each of the joints 520a, 520b, 520c, 525a, 525b, and 525c is configured to permit three-dimensional rotation. Herein, a ball 541 is installed at one link end, and a pedestal 542 for receiving the ball 541, at other link end. On the internal side of the pedestal 542, three layered piezoelectric elements 543a, 543b, and 543c are arranged in the form of an equilateral triangle at regular intervals. The free ends of the layered piezoelectric elements are placed closely to the surface of the ball 541 but oriented slightly outward of the center of the ball 541. Thus, an actuator mechanism is formed to selectively drive and brake bending.

The layered piezoelectric elements 543a, 543b, and 543c are controlled and driven by a brake actuator driving circuit 532 and an actuator driving circuit 534. In FIG. 58(A), the tips of the layered piezoelectric elements 543b and 543c are separated from the surface of the ball 541 or in a conducting or nonconducting state, so that the layered piezoelectric elements 543b and 543c will contract. On the other hand, the other layered piezoelectric element 543a is provided with alternating current to vibrate. The vibrating layered piezoelectric element 543a hits the surface of the ball 541 with its tip. The layered piezoelectric elements 543a, 543b, and 543c are oriented to the external periphery but not perpendicularly facing the surface of the ball 541. Therefore, the ball 541 rotates in the arrow direction in which the layered piezoelectric element 543a will duly land. Other layered piezoelectric elements 543b and 543c are contracting and parting away from the surface of the ball 541, which, therefore, will not hinder the rotation of the ball.

In FIG. 58(B), all the layered piezoelectric elements 543a, 543b, and 543c are conducting and stretching. Their tips are pressed on the surface of the ball 541. In this state, the ball 541 will not rotate because of the brake by the layered piezoelectric elements 543a, 543b, and 543c. Even if part of the layered piezoelectric elements 543a, 543b, and 543c is conducting and stretching, the brake will be activated.

In FIG. 58(C), two layered piezoelectric elements 543a and 543c are conducting or nonconducting to contract. Their tips are placed apart from the surface of the ball 541. On the other hand, other layered piezoelectric element 543b is provided with alternating current to vibrate. When the tip of the vibrating layered piezoelectric element 543b hits the surface of the ball 541, the ball rotates in the arrow direction in which the layered piezoelectric element 543b will duly land. Thus, a rotating direction or a bending direction can be determined by selecting at least one of layered piezoelectric elements 543a, 543b, and 543c.

As shown in FIG. 57(A), a permanent magnet 546 is mounted on the surface of a ball 541 of each joint 520a, 520b, 520c, 525a, 525b, or 525c. Three or more Hall elements 547 are mounted on the internal surface of a pedestal 542, facing the permanent magnet. When the joint 520a, 520b, 520c, 525a, 525b, or 525c bends, the permanent magnet 546 on the surface of the ball 541 is dislocated from the Hall elements 547 according to the bending rate. Then, the Hall elements 547 vary their output values depending on the bending direction. Potentiometers a, b, and c are formed so to detect the bending directions of the joints 520a, 520b, 520c, 525a, 525b, and 525c, and their bending rates.

FIG. 59 shows various examples of treatment adapters 523 for an intracorporeal treatment apparatus 511. A treatment adapter most suitable for a treated lesion will be selected for use. A treatment adapter 523 of FIG. 59(A) has a built-in laser probe 351, which emits a laser beam to dissect tissues. The tip side of the treatment adapter 523 is provided with a strain sensor 552 from which a line 553 made of a super elastic alloy is extending to form an antenna 554. When the antenna 554 senses the surface of a lesion, a distance of the laser probe 551 from the surface (or a feed of the laser probe) is determined.

Figure 59A:
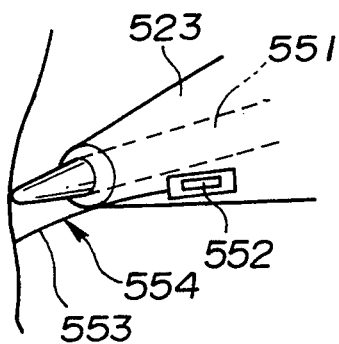
FIGS. 59(a), 59(b), 59(c) and 59(d) are explanatory diagrams of treatment adapters for the intracorporeal treatment apparatus.
Figure 59B:
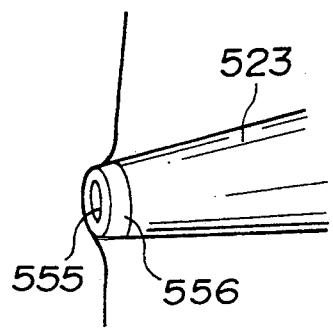

A treatment adapter 523 of FIG. 59(B) has a built-in water jet scalpel nozzle 555 which dissects tissues. This treatment adapter 523 has a pressure sensitive sensor 556 at its tip.

Figure 59C:
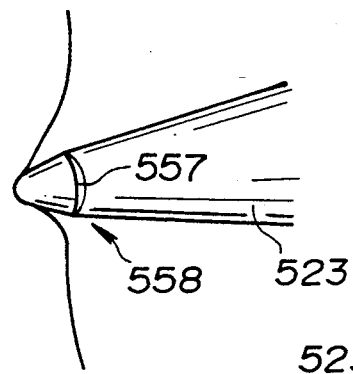

A treatment adapter 523 of FIG. 59(C) has an electrode 557 at its tip, thus forming an electric scalpel 558.

Figure 59D:
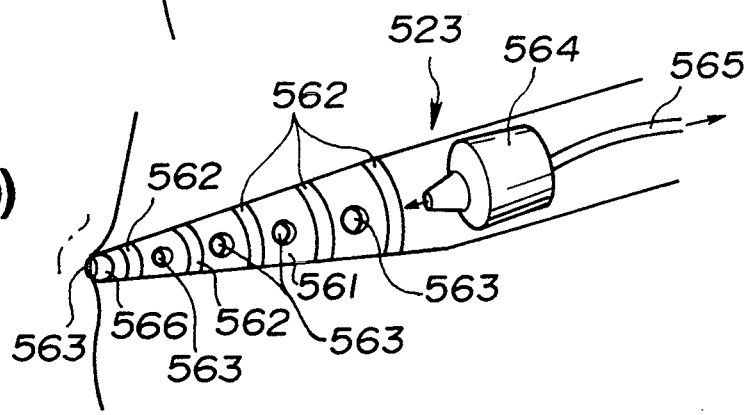

A treatment adapter 523 of FIG. 59(D) forms a perforated electric probe. Multiple small ring electrodes 562 are installed at regular intervals on the side circumference of a conical probe body 561, and medicine injection holes 563 are formed between the ring electrodes 562 and at the tip of the probe body 561. A micro-pump 564 incorporated in the probe body 561 feeds anti-cancer agent or other medicine supplied from a reservoir, which is not shown, through a tube 565. The tip of the probe body 561 is provided with a pressure sensitive sensor 566. This treatment adapter 523 serving as a perforated electric probe is inserted into, for example, a cancerous lesion. Then, high voltage is supplied instantaneously between the ring electrodes 562. After that or after and before that, the micro-pump 564 pumps in anti-cancer agent intermittently. Thereby, a cancer cell is holed and anti-cancer agent is injected at the same time. This provides improved therapeutic effects.

Next, the operating procedure of an intracorporeal treatment apparatus will be described. First, a surgeon holds a grasping section 529 of a master arm 518 as shown in FIGS. 53 and 55. While viewing a TV monitor 515, the surgeon drives an intracorporeal treatment arm 517 in master-slave mode. An electronic control circuit 516 allows the treatment arm 517 to move in association with the master arm 518 with a proportionally reduced moving force. Then, the surgeon places the tip of a treatment adapter 523 on the surface of a lesion to carry out profiling. During the profiling, the tip of the treatment adapter 523 is pressed until the output of a touch sensor 524 will be stabilized. When the output of the touch sensor 524 exceeds a certain level, brake actuators α, β, and γ inside joints 525a, 525b, and 525c of the master arm 518 start working to discourage the movement of the master arm 518. The surgeon profiles the surface of the lesion while feeling the discouraged movement of the master arm 518.

During the profiling, detection signals sent from potentiometers a, b, and c are received by a position detecting circuit 533 and stored as profile information in a storage circuit 536. After the shape of the surface of the lesion has thus been stored, 2 mm, for example, is entered as a feed for feeding the treatment adapter 523 beyond the profiling position. Then, a feed setting circuit 537 sends the value to an arithmetic logic unit 535. The stored profile information is used to drive the treatment arm 517. Consequently, the treatment art 517 dissects the lesion at the depth of the feed.

Figure 60A:
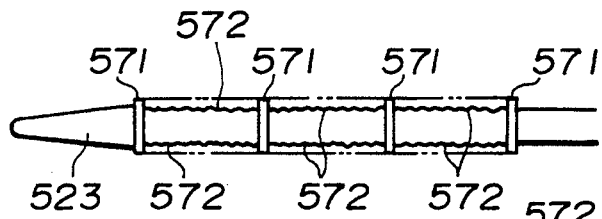
FIGS. 60(a) and 60(b) are explanatory diagrams showing the first variant of an arm of the intracorporeal treatment apparatus.
Figure 60B:
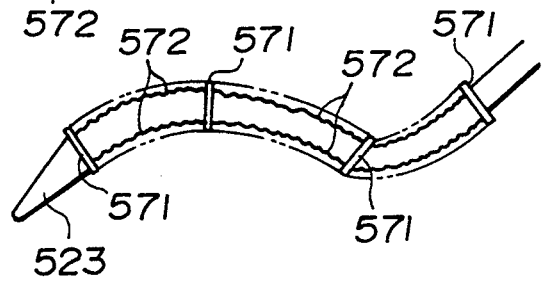
Figure 61A:
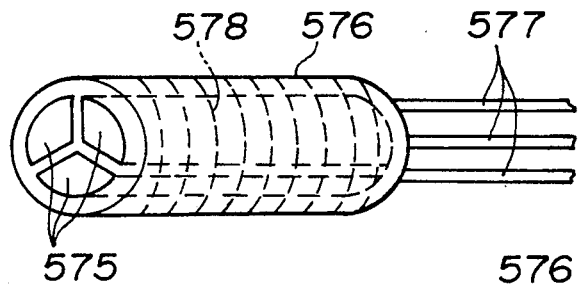
FIGS. 61(a) and 61(b) are explanatory diagrams showing the second variant of the arm of the intracorporeal treatment apparatus.
Figure 61B:
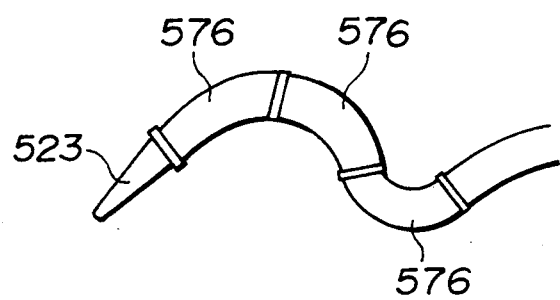

FIGS. 60, 61, and 62 show other examples of arms usable instead of the aforesaid arms 517 and 518. In an arm of FIG. 60, a wire 572 made of multiple shape memory alloys is laid out to connect joint members 571. When the wires 572 are selectively heated using a conducting resistance heat generating means, the wires 572 contract. Accordingly, the arm bends in the contracting direction. FIG. 60(A) shows the state of the arm before heating. FIG. 60(B) shows the state of the arm heated to bend.

In FIG. 61, multiple perforated tubes 576 each having multiple sealed bores 575 arranged in parallel in the longitudinal direction are set in array. Each bore 575 is connected to an air tube 577 independently. When a selected bore 575 is aerated through the air tube 577, the portion of the aerated bore 575 warps to bend the arm towards the reverse side. Fibers 578 for preventing excessive dilatation are mixed in the wall of each perforated tube 576.

Figure 62A:
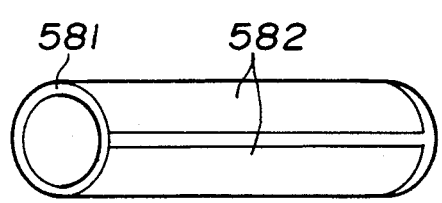
FIGS. 62(a) and 62(b) are explanatory diagrams showing the third variant of the arm of the intracorporeal treatment apparatus.
Figure 62B:
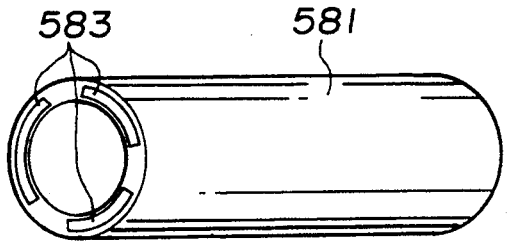

In FIG. 62(A), piezoelectric polymer material 582 is coated on three portions of a flexible tube 581. In FIG. 62(B), three liquid crystals 583 are embedded separately in the wall of the flexible tube 581. Multiple tubes 581 of this kind are coupled in the axial direction. Then, an electrode, which is not shown, is formed on each portion of piezoelectric polymer material 582 or each liquid crystal 583 so that voltage can apply independently. The piezoelectric polymer material 582 or liquid crystal 583 stretches reversibly according to the voltage supplied. When any selected portion of piezoelectric polymer material 582 or any selected liquid crystal 583 is energized, the flexible tube 581 bends. Flexible tubes of this kind are coupled to form an arm.

The aforesaid intracorporeal treatment apparatus comprises the following means: an intracorporeal insertion treatment section formed with an articulated arm having a treatment adapter and a touch sensor at its tip, an operation arm for moving the articulated arm with a 1-to-1 ratio of moving force or with a proportional moving force, a means for driving the actuators of joints of the treatment arm according to a signal sent from a sensor for detecting the driving rates of the joints of the operation arm, a means for storing the driving rates of the joints, a means for arithmetically calculating the actuator driving rates of the joints of the treatment arm by adding the treatment workload of the treatment adapter to the stored driving rates, and a means for driving the treatment arm according to the arithmetically calculated rates.

Each of the foregoing joints is made up of a ball coupler, three piezoelectric actuators installed opposing the ball surface of the ball coupler, and means for energizing the piezoelectric actuators independently.

The aforesaid arm is not restricted to articulated arms which bend at multiple points or joints, but may include arms which bend partly or entirely. Any arm can apply as far as it warps and bends.

Some of the aforesaid embodiments may be combined to form different embodiments which also belong to the present invention.

What is claimed is:

1. A medical system, comprising:
   a medical apparatus for applying medical care to a subject and including an operation unit that a surgeon manipulates and a treatment section located away from and operably connected to said operation unit to treat the subject in association with the manipulation of said operation unit, wherein said treatment section includes a treatment adapting means for grasping or resecting an examined region of the subject; an observation means for observing at least a state of contact between said treatment section formed in the distal portion of said medical apparatus and the examined region of the subject to be treated with said treatment section, wherein said observation means includes an endoscope having an objective optical system in the distal portion of an elongated insertion tube;
   a detecting means operably connected to said treatment adapting means for detecting a state of contact between said treatment section and the subject; and
   a reproducing means operably connected to said operation unit for reproducing the state of contact according to an output of said detecting means so that the surgeon can tactilely perceive the state of contact.

2. A medical system according to claim 1, wherein said reproducing means is an amplification reproducing means for amplifying and reproducing the state of contact so that the surgeon can tactilely perceive the state of contact.

3. A medical system according to claim 1, wherein said endoscope includes a channel and said treatment adapting means runs through said channel.

4. A medical system according to claim 1, wherein said objective optical system includes a solid-state imaging device for photoelectrically transferring optical images formed by the objective optical system.

5. A medical system according to claim 4, further comprising a monitor for displaying images relative to said optical images that said solid-state imaging device transfers photoelectrically.

6. A medical system according to claim 1, wherein said detecting means includes a contact force detecting means for detecting a contact force acting on said treatment section when said treatment section touches the subject, and said reproducing means amplifies a contact force detected by said contact force detecting means and feeds back said contact force so that an operation member of said operation unit which is manipulated to perform grasping or resection using said treatment section will be driven negatively to the manipulation for increasing said contact force.

7. A medical system according to claim 1, further comprising a tension detecting means for detecting a tension acting on said treatment section when said treatment section touches said subject, wherein said reproducing means amplifies a tension detected by said tension detecting means and feeds back said tension so that a grasping operation member of said operation unit will be driven negatively to the manipulation for increasing the tension.

8. A medical system according to claim 1, further comprising a manipulation rate detecting means for detecting a manipulation rate at which the surgeon manipulates said operation unit.

9. A medical system according to claim 8, wherein said operation unit comprises a movable member and wherein said manipulation rate detecting means detects a moving rate of said movable member for operating said treatment section formed in said operation unit.

10. A medical system according to claim 8 wherein said manipulation rate detecting means includes a rotary encoder.

11. A medical system according to claim 8 wherein said manipulation rate detecting means includes a treatment section driving means for moving said treatment section according to an output of said manipulation rate detecting means.

12. A medical system according to claim 11 wherein said treatment section driving means includes a motor.

13. A medical system according to claim 11, further comprising a converting means for establishing a proportional relationship between a manipulation rate detected by said manipulation rate detecting means and an operation rate of operating said treatment section.

14. A medical system according to claim 13, further comprising a changing means for changing said relationship established by said converting means.

15. A medical system according to claim 1 further comprising a restricting means for restricting the operation of said operation unit according to an output of said detecting means.

* * * * *